United States Patent
Fujita et al.

(10) Patent No.: US 10,487,420 B2
(45) Date of Patent: Nov. 26, 2019

(54) SINGLE CRYSTAL OF POROUS COMPOUND, METHOD FOR ASSESSING QUALITY OF SINGLE CRYSTAL, METHOD FOR PREPARING SOLUTION INCLUDING COMPOUND TO BE ANALYZED, METHOD FOR PRODUCING CRYSTAL STRUCTURE ANALYSIS SAMPLE, AND METHOD FOR DETERMINING MOLECULAR STRUCTURE OF COMPOUND TO BE ANALYZED

(71) Applicant: The University of Tokyo, Tokyo (JP)

(72) Inventors: Makoto Fujita, Tokyo (JP); Yasuhide Inokuma, Tokyo (JP); Yuya Doumoto, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/556,930

(22) PCT Filed: Mar. 10, 2016

(86) PCT No.: PCT/JP2016/057656
§ 371 (c)(1),
(2) Date: Sep. 8, 2017

(87) PCT Pub. No.: WO2016/143872
PCT Pub. Date: Sep. 15, 2016

(65) Prior Publication Data
US 2018/0245239 A1 Aug. 30, 2018

(30) Foreign Application Priority Data
Mar. 10, 2015 (JP) ................................. 2015-047731

(51) Int. Cl.
C30B 29/54 (2006.01)
C07D 401/14 (2006.01)
(Continued)

(52) U.S. Cl.
CPC ............ *C30B 29/54* (2013.01); *C07D 401/14* (2013.01); *G01N 21/21* (2013.01); *G01N 23/20* (2013.01); *G01N 23/20008* (2013.01)

(58) Field of Classification Search
CPC .............................. C30B 29/54; C30B 33/00
See application file for complete search history.

(56) References Cited

U.S. PATENT DOCUMENTS

2015/0219533 A1   8/2015  Fujita et al.

FOREIGN PATENT DOCUMENTS

| JP | 11-199398 A | 7/1999 |
|---|---|---|
| JP | 2014-169265 A | 9/2014 |
| WO | 2014038221 A1 | 3/2014 |

OTHER PUBLICATIONS

"Excavations in molecular crsytals", Le Fur et al. Royal Soceity of Chemistry Chemical Communications 2003 296602967.*

(Continued)

*Primary Examiner* — Robert M Kunemund
(74) *Attorney, Agent, or Firm* — Westerman, Hattori, Daniels & Adrian, LLP

(57) ABSTRACT

The present invention provides a single crystal of a porous compound, the single crystal being used to produce a crystal structure analysis sample for a compound to be analyzed by contacting the single crystal of the porous compound having a three-dimensional framework and three-dimensionally regularly-arranged pores and/or hollows formed by being divided by the three-dimensional framework with a solution that includes the compound to be analyzed, and arranging molecules of the compound to be analyzed in a regular array in the pores and/or hollows. The single crystal of the porous compound are characterized in that: one side of the single crystal is 10 to 2000 μm; and the single crystal maintains monocrystalline properties even after the single crystal is (Continued)

placed in contact with a solvent that is chemically the same as the solvent of the solution that includes the compound to be analyzed.

7 Claims, 7 Drawing Sheets

(51) Int. Cl.
    *G01N 23/20*     (2018.01)
    *G01N 21/21*     (2006.01)
    *G01N 23/20008*     (2018.01)

(56) References Cited

OTHER PUBLICATIONS

Inokuma et al., "X-ray analysis on the nanogram to microgram scale using porous complexes," Nature, Mar. 28, 2013, vol. 495, No. 7442, pp. 461-466, cited in ISR.

Inokuma et al., "Crystalline Sponge Method—a crystal structure analysis that defies common wisdom," Chemistry vol. 68, pp. 35-40 (Aug. 2013), cited in the specification.

Van Der Sluis et al., "BYPASS: an Effective Method for the Refinement of Crystal Structures Containing Disordered Solvent Regions," Acta Crystallographica Section A: Foundations of Crystallography 46.3 (1990) pp. 194-201, cited in the specification.

Horike et al., "Fundamentals of Porous Coordination Polymers (PCP)/Metal-Organic Frameworks (MOF)," Material Matters No. 7, Sigma-Aldrich (Sep. 2012) (16 pages), cited in the specification.

Neville et al., "A Family of Three-Dimensional Molecular Framework Materials Containing the Three-Connecting Ligands 2,4,6-Tris (n'-pyridyl)-1,3,5-triazine: 3-tpt and 4-tpt," Australian Journal of Chemistry 66.4 (2013), pp. 452-463, cited in the specification.

Yang et al. "Two Robust Porous Metal-Organic Frameworks Sustained by Distinct Catenation: Selective Gas Sorption and Single-Crystal-to-Single-Crystal Guest Exchange," Chemistry—An Asian Journal 5.11 (2010), pp. 2358-2368, cited in the specification.

International Search Report dated Jun. 7, 2016, issued in counterpart International Application No. PCT/JP2016/057656 (1 page).

Extended European Search Report, dated Jun. 18, 2019, issued in counterpart European Application No. 16761838.8 (in English; 9 pages).

Biradha, K. et al., "A Springlike 3D-Coordination Network That Shrinks or Swells in a Crystal-to-Crystal Manner upon Guest Removal or Readsorption", Angewandte Chemie, vol. 41, No. 18, Sep. 16, 2002, pp. 3392-3395 (in English; cited in EESR).

Nokuma, Y. et al., "Preparation and guest-uptake protocol for a porous complex useful for 'crystal-free' crystallography", Nature Protocols, vol. 9, No. 2, Jan. 9, 2014, pp. 246-252 (in English; cited in EESR).

\* cited by examiner

Case 1

Parallel shift operation → shape retention ratio of 100%

Case 2

Parallel shift operation →

Shape retention ratio of 9 %

Case 3

Suction and discharge operation →

Shape retention ratio of 98%

Case 4

Suction and discharge operation

Shape retention ratio of 4 %

Case 5

Parallel shift oeration

Shape retention ratio of 100%

Case 6

Parallel shift operation

Shape retention ratio of 10 %

Case 7

Suction and discharge operation →

Shape retention ratio of 100%

Case 8

Suction and discharge operation →

Shape retention ratio of 10 %

SINGLE CRYSTAL OF POROUS COMPOUND, METHOD FOR ASSESSING QUALITY OF SINGLE CRYSTAL, METHOD FOR PREPARING SOLUTION INCLUDING COMPOUND TO BE ANALYZED, METHOD FOR PRODUCING CRYSTAL STRUCTURE ANALYSIS SAMPLE, AND METHOD FOR DETERMINING MOLECULAR STRUCTURE OF COMPOUND TO BE ANALYZED

TECHNICAL FIELD

The present invention relates to a porous compound single crystal which is used when preparing a crystal structure analysis sample using so called "crystalline sponge method", a method for determination of whether a single crystal is good or bad, a method for producing a crystal structure analysis sample using a single crystal which is determined as a good crystal by the method for determination, a method for preparing an analysis target compound-containing solution which is used when preparing a crystal structure analysis sample using a crystalline sponge method, a method for producing a crystal structure analysis sample using an analysis target compound-containing solution obtained by the method for preparing the analysis target compound-containing solution, and a method for determining a molecular structure of an analysis target compound using a crystal structure analysis sample obtained by these methods.

BACKGROUND ART

In recent years, a method using a crystalline sponge method has attracted attention. When a crystal structure analysis sample is produced using the crystalline sponge method, the crystal structure analysis sample is produced by providing a porous single crystal including of pores and/or voids, bringing the single crystal into contact with a solution of a compound whose molecular structure is to be determined (hereinafter, sometimes referred to as "analysis target compound") to introduce molecules of the analysis target compound into pores and/or the voids of the single crystal so that the molecules of the analysis target compound are arranged in an ordered manner.

Specifically, Non-Patent Literature 1 discloses a method for producing a crystal structure analysis sample using a porous single crystal of a macromolecular metal complex as a crystalline sponge to introduce a flavonoid and the like into the pores of the porous single crystal.

As described above, by using the crystalline sponge method, it is possible to prepare a crystal structure analysis sample without preparing a single crystal of an analysis target compound. Thus, by using the crystalline sponge method, even when an analysis target compound is liquid or gas under normal conditions, it is possible to prepare a crystal structure analysis sample.

Further, when the crystalline sponge method is used, a crystal structure analysis sample can be prepared with a trace amount of an analysis target compound. Thus, by using the crystalline sponge method, it is possible to prepare a sample for crystal structure analysis efficiently even when an analysis target compound is a compound that is not easily available in a large amount (e.g., impurities in natural products or metabolites and the like).

CITATION LIST

Non-Patent Literature

Non-Patent Literature 1: Monthly magazine named *CHEMISTRY* 68, August issue, 35-40 (2013)

SUMMARY OF INVENTION

Technical Problem

As described above, by using the crystalline sponge method, a crystal structure analysis sample can be prepared with a far less amount of analysis target compound than that used in a method in which a single crystal of the analysis target compound is prepared.

However, even when a single crystal having fine external appearance is used as a crystalline sponge, the single crystal sometimes loses single crystallinity while the single crystal stays in contact with a solution containing an analysis target compound, and thus a crystal structure analysis sample of good quality cannot be obtained. Thus, for performing crystal structure analysis more reliably, it is required that an analysis target compound is provided to a certain extent to prepare two or more crystal structure analysis samples. Therefore, a method which can produce a crystal structure analysis sample of good quality more reliably has been desired.

The invention was conceived in view of the prior arts. An object of the invention is to provide a porous compound single crystal which makes it possible to produce a crystal structure analysis sample of good quality more reliably by using a crystalline sponge method, a method for determination of whether a single crystal is good or bad, a method for producing a crystal structure analysis sample using a single crystal which is determined as good or bad by the method for determination, a method for preparing an analysis target compound-containing solution which makes it possible to produce a crystal structure analysis sample of good quality more reliably by using a crystalline sponge method, a method for producing a crystal structure analysis sample using an analysis target compound-containing solution obtained by the method for preparing the analysis target compound-containing solution, and a method for determining a molecular structure of an analysis target compound using a crystal structure analysis sample obtained by these methods.

Solution to Problem

The inventors conducted extensive studies, in order to solve the above problem, with respect to stability of a single crystal when the single crystal is brought in contact with an analysis target compound-containing solution. As a result, the inventors found that a solvent of the analysis target compound-containing solution has an influence on stability of single crystallinity, and that a crystal structure analysis sample of good quality can be obtained more reliably by the following steps: bringing single crystals into contact with a solvent which is chemically identical to the solvent of the analysis target compound-containing solution in advance of bringing the single crystals into contact with the analysis target compound-containing solution, and using a single crystal maintaining single crystallinity even after the contact of the single crystal with the solvent, which is chemically identical to the solvent of the analysis target compound-containing solution, as a crystalline sponge. These findings have led to the completion of the invention.

Several aspects of the invention provide the following single crystals of a porous compound (see [1] to [4]), methods for determination of whether a single crystal is good or bad (see [5] to [9]), methods for producing a crystal structure analysis sample (see [10] and [17]), methods for preparing a solution containing an analysis target compound (see [11] to [15]), and methods for determining a molecular structure of an analysis target compound (see [18]).

[1] A porous compound single crystal used for producing a crystal structure analysis sample of an analysis target compound by bringing the porous compound single crystal having a three-dimensional framework, and having pores and/or voids, which are defined by the three-dimensional framework, that are three-dimensionally arranged in an ordered manner into contact with an analysis target compound-containing solution to arrange molecules of the analysis target compound in the pores and/or the voids in an ordered manner, wherein the length of one side of the single crystal is 10 to 2000 µm, and the single crystal maintains single crystallinity even after bringing the single crystal into contact with a solvent which is chemically identical to the solvent of the analysis target compound-containing solution.

[2] The single crystal according to [1], wherein the rate of change in absorbance of UV-vis absorption spectrum of the single crystal within the wavelength range of 450 to 500 nm is 10% or less between before and after bringing the single crystal into contact with the solvent which is chemically identical to the solvent of the analysis target compound-containing solution.

[3] The single crystal according to [1], wherein shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in a solvent which is chemically identical to the solvent of the analysis target compound-containing solution at a liquid depth of 5 mm.

[4] The single crystal according to [1], wherein shape retention ratio of the single crystal is 90% or more between before and after an operation of sucking a solution containing the single crystal and a solvent which is chemically identical to the solvent of the analysis target compound-containing solution at a suction rate of 6 µL/sec using a pipet tip for 20 to 200 µL having an aperture of 250 µm in diameter at a liquid depth of 5 mm, and then discharging the solution containing the single crystal at a discharge rate of 6 µL/sec.

[5] A method for determination of whether a single crystal used for producing a crystal structure analysis sample of an analysis target compound is good or bad by bringing the porous compound single crystal having a three-dimensional framework, and having either or both of pores and voids, which are defined by the three-dimensional framework, that are three-dimensionally arranged in an ordered manner into contact with an analysis target compound-containing solution to arrange molecules of the analysis target compound in the pores and/or the voids in an ordered manner, comprising step (A1): bringing the single crystal into contact with a solvent which is chemically identical to the solvent of the analysis target compound-containing solution; and step (A2): when the single crystal is confirmed to maintain single crystallinity even after the contact of the single crystal with the solvent in step (A1), determining the single crystal as suitable for producing the crystal structure analysis sample.

[6] The method for determination of whether a single crystal is good or bad according to [5], wherein the method for confirming the single crystal as maintaining single crystallinity in step (A2) comprises:

confirming the absence of color irregularities or brightness irregularities in the porous compound single crystal by crossed Nicols observation of the porous compound single crystal using a polarization microscope.

[7] The method for determination of whether a single crystal is good or bad according to [5], wherein the method for confirming the single crystal as maintaining single crystallinity in step (A2) comprises:

confirming that the rate of change in absorbance of UV-vis absorption spectrum of the single crystal within the wavelength range of 450 to 500 nm is 10% or less between before and after bringing the single crystal into contact with the solvent which is chemically identical to the solvent of the analysis target compound-containing solution.

[8] The method for determination of whether a single crystal is good or bad according to [5], wherein the method for confirming the single crystal as maintaining single crystallinity in step (A2) comprises:

confirming that shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in a solvent which is chemically identical to the solvent of the analysis target compound-containing solution at a liquid depth of 5 mm.

[9] The method for determination of whether a single crystal is good or bad according to [5], wherein the method for confirming the single crystal as maintaining single crystallinity in step (A2) comprises:

confirming that shape retention ratio of the single crystal is 90% or more between before and after an operation of sucking a solution containing the single crystal and a solvent which is chemically identical to the solvent of the analysis target compound-containing solution at a suction rate of 6 µL/sec using a pipet tip for 20 to 200 µL having an aperture of 250 µm in diameter at a liquid depth of 5 mm, and then discharging the solution containing the single crystal at a discharge rate of 6 µL/sec.

[10] A method for producing a crystal structure analysis sample, comprising bringing the single crystal according to [1] into contact with an analysis target compound-containing solution to arrange molecules of the analysis target compound in the pores and/or the voids in an ordered manner.

[11] A method for preparing an analysis target compound-containing solution used for producing a crystal structure analysis sample of the analysis target compound by bringing a porous compound single crystal having a three-dimensional framework, and having pores and/or voids, which are defined by the three-dimensional framework, that are three-dimensionally arranged in an ordered manner into contact with the analysis target compound-containing solution to arrange molecules of the analysis target compound in the pores and/or the voids in an ordered manner, the method comprising step (B1): bringing the single crystal into contact with a solvent dissolving the analysis target compound, and step (B2): when the single crystal is confirmed to maintain single crystallinity even after the contact of the single crystal with the solvent in step (B1), determining the solvent as suitable for a solvent of the analysis target compound-containing solution used for producing the crystal structure analysis sample.

[12] The method for preparing an analysis target compound-containing solution according to [11], wherein the method for determining the solvent as suitable for the solvent of the analysis target compound-containing solution used for producing the crystal structure analysis sample in step (B2) comprises:

confirming the absence of color irregularities or brightness irregularities in the porous compound single crystal by crossed Nicols observation of the porous compound single crystal using a polarization microscope.

[13] The method for preparing an analysis target compound-containing solution according to [11], wherein the method for determining the solvent as suitable for the solvent of the analysis target compound-containing solution used for producing the crystal structure analysis sample in step (B2) comprises:

confirming that the rate of change in absorbance of UV-vis absorption spectrum of the single crystal within the wavelength range of 450 to 500 nm is 10% or less between before and after bringing the single crystal into contact with a solvent which is chemically identical to the solvent of the analysis target compound-containing solution.

[14] The method for preparing an analysis target compound-containing solution according to [11], wherein the method for determining the solvent as suitable for the solvent of the analysis target compound-containing solution used for producing the crystal structure analysis sample in step (B2) comprises:

confirming that shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in a solvent which is chemically identical to the solvent of the analysis target compound-containing solution at a liquid depth of 5 mm.

[15] The method for preparing an analysis target compound-containing solution according to [11], wherein the method for determining the solvent as suitable for the solvent of the analysis target compound-containing solution used for producing the crystal structure analysis sample in step (B2) comprises:

confirming that shape retention ratio of the single crystal is 90% or more between before and after an operation of sucking a solution containing the single crystal and a solvent which is chemically identical to the solvent of the analysis target compound-containing solution at a suction rate of 6 μL/sec using a pipet tip for 20 to 200 μL having an aperture of 250 μm in diameter at a liquid depth of 5 mm, and then discharging the solution containing the single crystal at a discharge rate of 6 μL/sec.

[16] A method for producing a crystal structure analysis sample, comprising bringing the single crystal according to [1] into contact with an analysis target compound-containing solution prepared by any one of the methods according to [11] to [15] to arrange molecules of an analysis target compound in the pores and/or the voids in an ordered manner.

[17] A method for producing a crystal structure analysis sample, comprising bringing a single crystal, which is confirmed to maintain single crystallinity by the method according to [5], into contact with an analysis target compound-containing solution to arrange molecules of an analysis target compound in the pores and/or the voids in an ordered manner.

[18] A method for determining a molecular structure of an analysis target compound, comprising performing crystal structure analysis using a crystal structure analysis sample obtained by a method for producing the crystal structure analysis sample according to [16] or [17].

DESCRIPTION OF EMBODIMENTS

Figure 1:
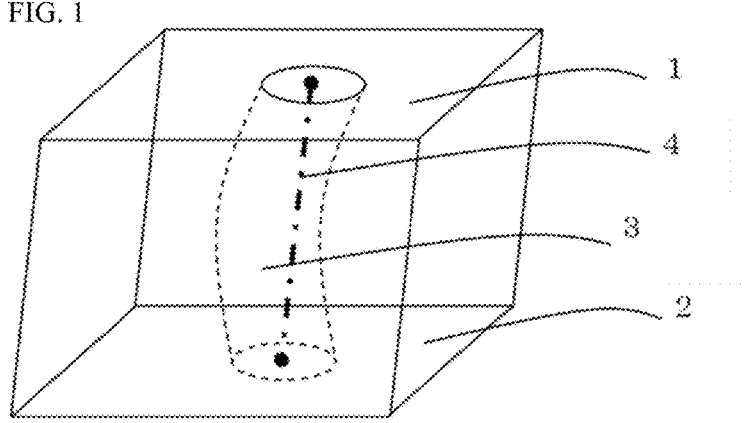
FIG. 1 illustrates the extension direction of a pore formed in a single crystal.

The invention is divided into sections of: a porous compound single crystal (embodiment number "1)"), a method for determination of whether a single crystal is good or bad (embodiment number "2)"), a method for producing a crystal structure analysis sample (embodiment number "3)"), a method for preparing an analysis target compound-containing solution (embodiment number "4)"), a method for producing a crystal structure analysis sample (embodiment number "5)"), and a method for determining a molecular structure of an analysis target compound (embodiment number "6)") according to the exemplary embodiments, and described in detail below.

1) Porous Compound Single Crystal

A porous compound single crystal of the invention comprises a single crystal used for producing a crystal structure analysis sample of an analysis target compound by bringing the porous compound single crystal having a three-dimensional framework, and having pores and/or voids, which are defined by the three-dimensional framework, that are three-dimensionally arranged in an ordered manner into contact with an analysis target compound-containing solution to arrange molecules of the analysis target compound in the pores and/or the voids in an ordered manner, wherein the length of one side of the single crystal is 10 to 2000 μm, and the single crystal maintains single crystallinity even after bringing the single crystal into contact with a solvent which is chemically identical to the solvent of the analysis target compound-containing solution.

The single crystal of the invention is preferably used for a technique of producing a crystal structure analysis sample of an analysis target compound by bringing such a porous compound single crystal having a three-dimensional framework, and having pores and/or voids, which are defined by the three-dimensional framework, that are three-dimensionally arranged in an ordered manner into contact with an analysis target compound-containing solution to arrange molecules of the analysis target compound in the pores and/or the voids in an ordered manner (so-called "crystalline sponge method").

[Porous Compound Single Crystal]

A porous compound single crystal used for the method of the invention (hereinafter sometimes referred to as "single crystal") internally has a three-dimensional framework, and has pores and/or voids, which are defined by the three-dimensional framework, that are three-dimensionally arranged in an ordered manner.

The three-dimensional framework refers to a framework-like structure that extends three-dimensionally within the single crystal. The three-dimensional framework includes one molecular chain, or two or more molecular chains, or includes one molecular chain, or two or more molecular chains, and a framework-forming compound.

The term "molecular chain" used herein refers to an assembly that is assembled by means of a covalent bond and/or a coordinate bond. The molecular chain may include a branched structure and a cyclic structure.

Examples of the three-dimensional framework that includes one molecular chain include a framework that is assembled in the form of a jungle gym.

The three-dimensional framework that includes two or more molecular chains refers to a framework in which all of two or more molecular chains are assembled into one unit by means of interactions (e.g., hydrogen bonds, π-π stacking interactions, and van der Waals forces). Examples of the three-dimensional framework include a framework in which two or more molecular chains are intertwined in the form of a puzzle ring. Examples of such a three-dimensional framework include the three-dimensional framework of the polynuclear metal complexes 1 and 2 described later.

The term "framework-forming compound" used herein refers to a compound that does not form part of a molecular chain, but forms part of a three-dimensional framework by means of interactions (e.g., hydrogen bonds, π-π stacking interactions, and van der Waals forces). Examples of the framework-forming compound include the framework-forming aromatic compound included in the polynuclear metal complex described later.

The expression "three-dimensionally arranged in an ordered manner" used herein in connection with pores and/or voids means that either or both of pores and voids are arranged in an ordered manner to such an extent that they can be observed by crystal structure analysis.

The term "pore" and "void" used herein refers to an internal space within a single crystal. An internal space that extends to have a tubular shape is referred to as "pore", and an internal space that does not fall under the term "pore" is referred to as "void".

The size of a pore has a correlation with the diameter of a circle that is inscribed to the pore (hereinafter may be referred to as "pore inscribed circle" or "inscribed circle") in a plane parallel to the crystal plane that is closest to a perpendicular plane with respect to the extension direction of the pore (hereinafter may be referred to as "parallel plane"). The size of a pore increases as the size of the inscribed circle increases, and decreases as the size of the inscribed circle decreases.

"The extension direction of a pore" may be determined as described below.

Specifically, a crystal plane X (e.g., a plane A, a plane B, a plane C, or a diagonal plane thereof) in an appropriate direction that intersects the target pore is selected. The atoms that are present in the crystal plane X and included in the three-dimensional framework are represented using the van der Waals radius to draw a cross-sectional view of the pore taken along the crystal plane X. Likewise, a cross-sectional view of the pore taken along a crystal plane Y that is shifted from the crystal plane X by one unit cell is drawn. Then, the center of the cross-sectional shape of the pore in the crystal plane X and the center of the cross-sectional shape of the pore in the crystal plane Y are connected by a straight line (dash-dotted line) (see FIG. 1). The direction of the straight line corresponds to the extension direction of the pore.

The diameter of the pore inscribed circle" may be determined as described below.

Specifically, a cross-sectional view of the pore taken along the parallel plane is drawn in a similar manner as described above. Then, the pore inscribed circle is drawn using the cross-sectional view, and the diameter of the pore inscribed circle is measured. The measured value is converted into the actual scale to determine the actual diameter of the pore inscribed circle.

The diameter of the pore inscribed circle in each parallel plane is measured while gradually shifting the parallel plane by one unit cell to determine the diameter of the smallest inscribed circle and the diameter of the largest inscribed circle.

The diameter of the pore inscribed circle of the single crystal is preferably 2 to 30 Å, and more preferably 3 to 10 Å.

When the shape of the pore significantly differs from a true circle, it is preferable to predict the inclusion capability of the single crystal from the minor axis and the major axis of the pore inscribed ellipse in the parallel plane.

The major axis of the pore inscribed ellipse of the single crystal is preferably 2 to 30 Å, and more preferably 3 to 10 Å. The minor axis of the pore inscribed ellipse of the single crystal is preferably 2 to 30 Å, and more preferably 3 to 10 Å.

The pore volume in the single crystal may be calculated using the method described in Acta Crystallogr. A46, 194-201 (1990) (hereinafter referred to as "Literature (A)"). Specifically, the pore volume in the single crystal may be calculated using the expression "volume of single crystal× void ratio in unit cell" based on the solvent accessible void (void volume in unit cell) calculated by a calculation program "PLATON SQUEEZE PROGRAM".

The pore volume in the single crystal (i.e., the total pore volume in one piece of the single crystal) is preferably $1\times10^{-7}$ to $0.1$ mm$^3$, and more preferably $1\times10^{-5}$ to $1\times10^{-3}$ mm$^3$.

When the single crystal has voids, the size of each void may be calculated using the method described in Literature (A) in a similar manner to the pore volume.

It is preferable that the single crystal be in the shape of a cube or a rectangular parallelepiped. The length of one side of the single crystal is preferably 10 to 2000 μm, and more preferably 60 to 200 μm. A high-quality crystal structure analysis sample can be easily obtained by utilizing a single crystal having such a shape and size.

The single crystal that is used to produce the crystal structure analysis sample may include only the three-dimensional framework (so-called host molecule), or may include the three-dimensional framework, and a replaceable molecule (so-called guest molecule) that is included in the pores and/or the voids.

It is preferable that the single crystal be designed so that the molecular structure can be determined with a resolution of at least 1.5 Å by applying MoKα radiation (wavelength: 0.71 Å) generated at a tube voltage of 24 kV and a tube current of 50 mA to the single crystal, and detecting the diffracted X-rays using a CCD detector. A high-quality crystal structure analysis sample can be easily obtained by utilizing a single crystal having such characteristics.

The single crystal is not particularly limited as long as the single crystal has the pores and/or the voids. Examples of the porous compound single crystal include a single crystal of a polynuclear metal complex, a urea crystal, and the like. Among these, a crystal of a polynuclear metal complex is preferable since it is possible to easily control the size of the pores and the voids, and the environment (e.g., polarity) within the pores and the voids.

Examples of the polynuclear metal complex include a polynuclear metal complex that includes a plurality of ligands having two or more coordinating moieties, and a plurality of metal ions that serve as the center metal.

The ligand having two or more coordinating moieties (hereinafter may be referred to as "multidentate ligand") is not particularly limited as long as the ligand can form the three-dimensional framework. A known multidentate ligand may be used as the ligand.

The term "coordinating moiety" used herein refers to an atom or an atomic group included in the ligand that has an unshared electron pair that can form a coordinate bond. Examples of the coordinating moiety include a hetero atom such as a nitrogen atom, an oxygen atom, a sulfur atom, and a phosphorus atom; an atomic group such as a nitro group, an amino group, a cyano group, and a carboxyl group; and the like. Among these, a nitrogen atom and an atomic group that includes a nitrogen atom are preferable.

It is preferable that the multidentate ligand include an aromatic ring since the planarity of the ligand is improved, and a strong three-dimensional framework is easily formed.

A single crystal of a polynuclear metal complex having relatively large pores and voids is normally obtained by utilizing a multidentate ligand in which the distance from the center of the ligand to the coordinating moiety is long, and a single crystal of a polynuclear metal complex having relatively small pores and voids is normally obtained by utilizing a multidentate ligand in which the distance from the center of the ligand to the coordinating moiety is short.

Since it is possible to easily obtain a single crystal having relatively large pores and voids, it is preferable to use a multidentate ligand having two or more coordinating moieties, more preferably a multidentate ligand having three coordinating moieties (hereinafter may be referred to as "tridentate ligand"), and still more preferably a tridentate ligand in which the unshared electron pairs (orbitals) of the three coordinating moieties are present in the same plane, and the three coordinating moieties are arranged radially with respect to the center of the tridentate ligand at an equal interval.

The expression "present in the same plane" used herein includes a case where each unshared electron pair is present in the same plane, and a case where each unshared electron pair is present in a plane that is shifted to some extent (e.g., present in a plane that intersects a reference plane at an angle of 20° or less).

The expression "three coordinating moieties are arranged radially with respect to the center of the tridentate ligand at an equal interval" used herein means that the three coordinating moieties are arranged on lines that extend radially from the center of the ligand at an equal interval, at an almost equal distance from the center of the ligand.

Examples of the tridentate ligand include a ligand represented by the following formula (1):

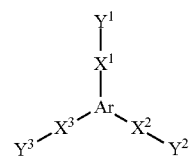

(1)

wherein Ar is a substituted or unsubstituted trivalent aromatic group, $X^1$ to $X^3$ are independently a divalent organic group, or a single bond that directly bonds Ar and $Y^1$, $Y^2$, or $Y^3$, and $Y^1$ to $Y^3$ are independently a monovalent organic group having a coordinating moiety.

Ar in the formula (1) is a trivalent aromatic group.

The number of carbon atoms included in Ar is normally 3 to 22, preferably 3 to 13, and more preferably 3 to 6.

Examples of Ar include a trivalent aromatic group having a monocyclic structure that includes one 6-membered aromatic ring.

Examples of the trivalent aromatic group having a monocyclic structure that includes one 6-membered aromatic ring include the groups respectively represented by the following formulas (2a) to (2d). Note that "*" in the formulas (2a) to (2d) indicates the position at which $X^1$, $X^2$, or $X^3$ is bonded.

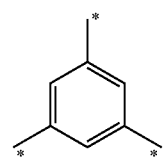

(2a)

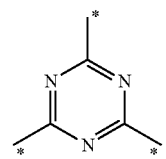

(2b)

-continued (2c)
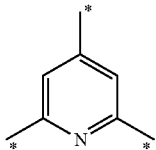

(2d)
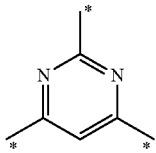

Ar can be aromatic groups represented by the formulas (2a) and (2c) to (2d) which may be substituted with a substituent at an arbitrary position. Examples of the substituent include an alkyl group such as a methyl group, an ethyl group, an isopropyl group, an n-propyl group, and a t-butyl group; an alkoxy group such as a methoxy group, an ethoxy group, an n-propoxy group, and an n-butoxy group; a halogen atom such as a fluorine atom, a chlorine atom, and a bromine atom; and the like. Ar is preferably the aromatic group represented by the formula (2a) or (2b), and particularly preferably the aromatic group represented by the formula (2b).

$X^1$ to $X^3$ are independently a divalent organic group, or a single bond that directly bonds Ar and $Y^1$, $Y^2$, or $Y^3$.

The divalent organic group is preferably a group that can form a π electron conjugated system together with Ar. When the divalent organic group represented by $X^1$ to $X^3$ forms a π electron conjugated system, the planarity of the tridentate ligand represented by the formula (1) is improved, and a strong three-dimensional network structure can be easily formed.

The number of carbon atoms included in the divalent organic group is preferably 2 to 18, more preferably 2 to 12, and still more preferably 2 to 6.

Examples of the divalent organic group include a divalent unsaturated aliphatic group having 2 to 10 carbon atoms, a divalent organic group having a monocyclic structure that consists of one 6-membered aromatic ring, a divalent organic group having a fused ring structure in which two to four 6-membered aromatic rings are fused, an amide group (—C(═O)—NH—), an ester group (—C(═O)—O—), a combination of two or more divalent organic groups among these divalent organic groups, and the like.

Examples of the divalent unsaturated aliphatic group having 2 to 10 carbon atoms include a vinylene group, an acetylene group (ethynylene group), and the like.

Examples of the divalent organic group having a monocyclic structure that includes one 6-membered aromatic ring, include a 1,4-phenylene group and the like.

Examples of the divalent organic group having a fused ring structure in which two to four 6-membered aromatic rings are fused, include a 1,4-naphthylene group, an anthracene-1,4-diyl group, and the like.

Examples of a combination of two or more divalent organic groups among these divalent organic groups include the groups respectively represented by the following formulas.

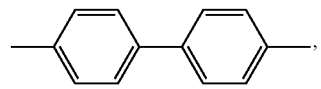

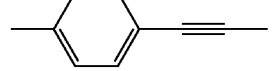

These aromatic rings may include a hetero atom (e.g., nitrogen atom, oxygen atom, and sulfur atom) in their ring.

The divalent organic group may be substituted with a substituent. Examples of the substituent include those mentioned above in connection with Ar.

Among them, the groups respectively represented by the following formulas are preferable as the divalent organic group that may be represented by $X^1$ to $X^3$.

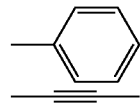 , 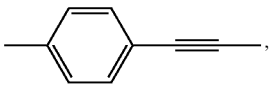 , $Y^1$ to $Y^3$ are independently a monovalent organic group having a coordinating moiety.

The organic group represented by $Y^1$ to $Y^3$ is preferably a group that can form a π electron conjugated system together with Ar and $X^1$ to $X^3$.

When the organic group represented by $Y^1$ to $Y^3$ forms a π electron conjugated system, the planarity of the tridentate ligand represented by the formula (1) is improved, and a strong three-dimensional framework can be easily formed.

The number of carbon atoms included in the organic group represented by $Y^1$ to $Y^3$ is preferably 5 to 11, and more preferably 5 to 7.

Examples of the organic group represented by $Y^1$ to $Y^3$ include the organic groups respectively represented by the following formulas (3a) to (3o). Note that "*" in the formulas (3a) to (3o) indicates the position at which $X^1$, $X^2$, or $X^3$ is bonded.

(3a)
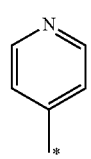

(3b)
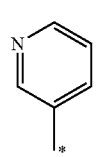

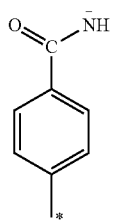

(3c)

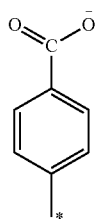

(3d)

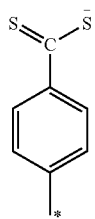

(3e)

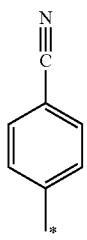

(3f)

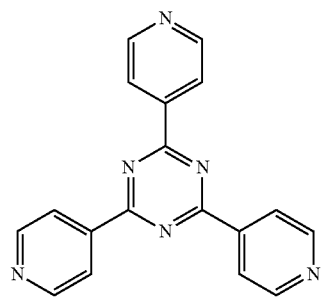

(4a)

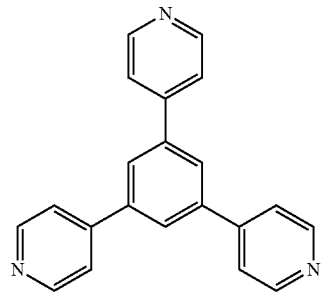

(4b)

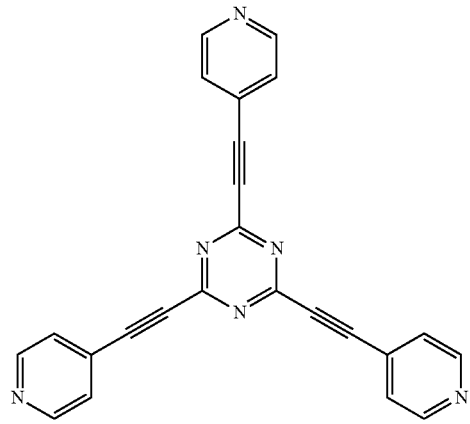

(4c)

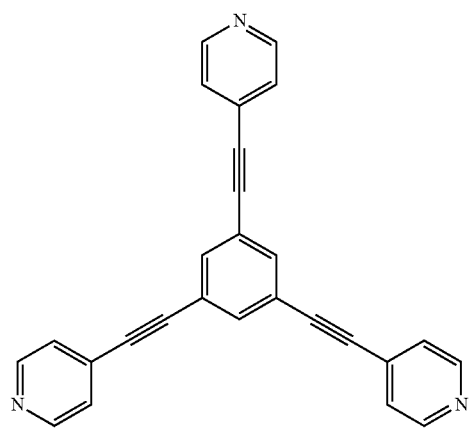

(4d)

$Y^1$ to $Y^3$ can be organic groups represented by the formulas (3a) to (3f) which may be substituted with a substituent at an arbitrary position. Examples of the substituent include those mentioned above in connection with Ar.

The group represented by the formula (3a) is particularly preferable as $Y^1$ to $Y^3$.

The size of the pores and the voids of the single crystal can be adjusted by appropriately selecting Ar, $X^1$ to $X^3$, and $Y^1$ to $Y^3$ in the tridentate ligand represented by the formula (1). This makes it possible to efficiently obtain a single crystal that has pores and voids having a size sufficient to include the desired molecule.

It is preferable that the tridentate ligand represented by the formula (1) have high planarity and high symmetry, and have a structure in which a π-conjugated system extends over the entire ligand, since a strong three-dimensional framework is easily formed. Examples of such a tridentate ligand include the ligands respectively represented by the following formulas (4a) to (4j).

(4e)
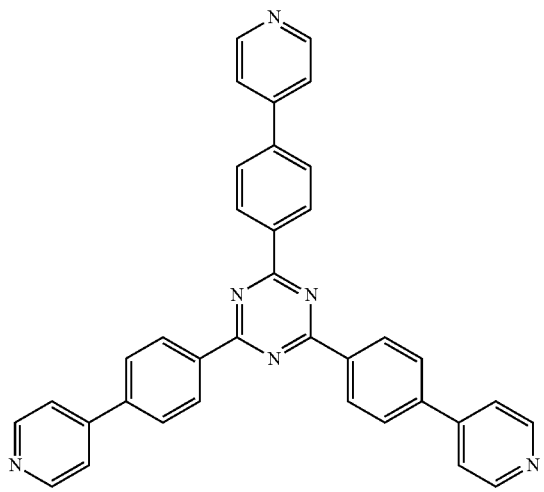

(4f)
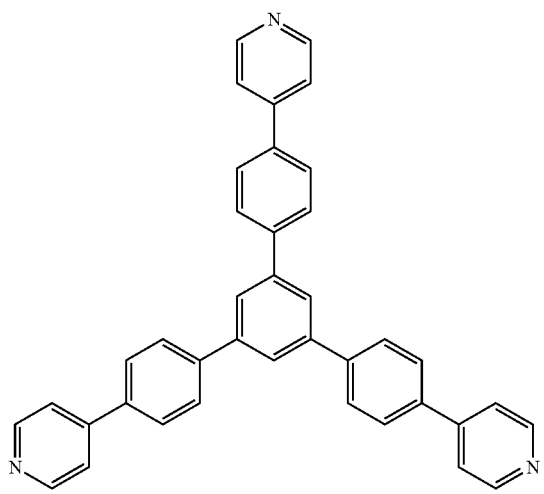

(4g)
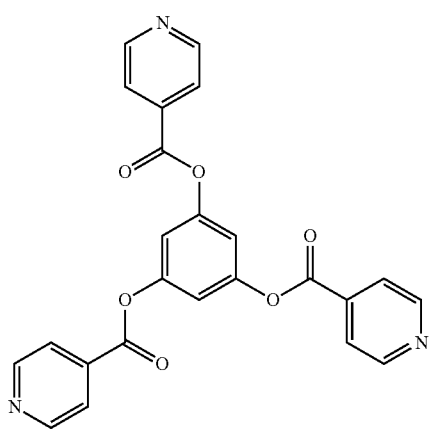

(4h)
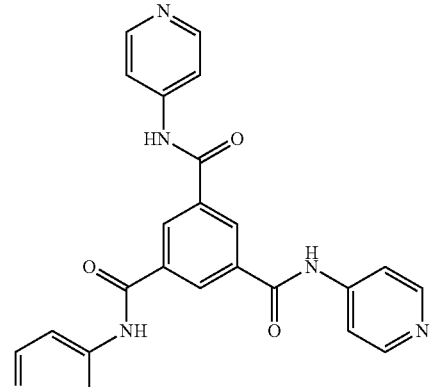

(4i)
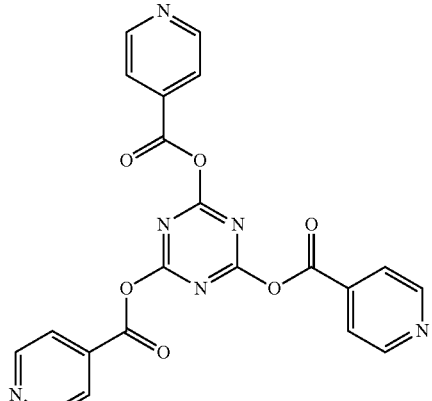

(4j)
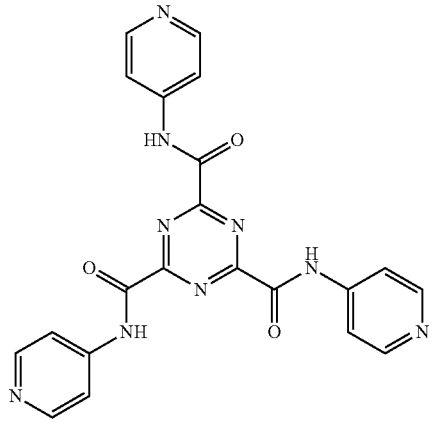

A commercially-available product may also be used as the multidentate ligand of the polynuclear metal complex. For example, Material Matters No. 7—Fundamentals of Porous Coordination Polymers (PCP)/Metal-Organic Frameworks (MOF) (September, 2012) published by Sigma-Aldrich lists pyrazine, 1,4-diazabicyclo [2.2.2]octane, 1,2-di(4-pyridyl) ethylene, 4,4'-bipyridyl, 4,4'-biphenyldicarboxylic acid, benzene-1,3-dicarboxylic acid, pyrazine-2,3-dicarboxylic acid, pyrazine-3,5-dicarboxylic acid, and the like as a PCP/MOF ligand and a linker compound. These compounds may be used as the multidentate ligand of the polynuclear metal complex.

The metal ion that serves as the center metal of the polynuclear metal complex is not particularly limited as long as the metal ion forms a coordinate bond together with the multidentate ligand to form the three-dimensional framework. It is preferable to use an ion of a metal that belongs to Groups 8 to 12 in the periodic table, such as an iron ion, a cobalt ion, a nickel ion, a copper ion, a zinc ion, a silver ion, a palladium ion, a ruthenium ion, a rhodium ion, and a platinum ion, and more preferably a divalent ion of a metal that belongs to Groups 8 to 12 in the periodic table. It is particularly preferable to use a zinc(II) ion or a cobalt(II) ion since a single crystal having large pores and voids can be easily obtained.

A monodentate ligand may be coordinated to the center metal of the polynuclear metal complex in addition to the multidentate ligand. Examples of the monodentate ligand include a monovalent anion such as a chloride ion (Cl⁻), a bromide ion (Br⁻), an iodide ion (I⁻), and a thiocyanate ion (SCN⁻); an electrically neutral coordinating compound such as ammonia, a monoalkylamine, a dialkylamine, a trialkylamine, and ethylenediamine; and the like.

The polynuclear metal complex may include a reaction solvent (i.e., a solvent used to synthesize the polynuclear metal complex), a replacement solvent (i.e., a solvent with which the reaction solvent is replaced (hereinafter the same)), and a framework-forming aromatic compound (described later).

The term "framework-forming aromatic compound" used herein refers to an aromatic compound that interacts with the molecular chain that forms the three-dimensional framework (excluding formation of a covalent bond and a coordinate bond as the interaction) to form part of the three-dimensional framework.

When the polynuclear metal complex includes the framework-forming aromatic compound, a stronger three-dimensional framework can be easily obtained, and the three-dimensional framework may be further stabilized even in a state in which the polynuclear metal complex includes the molecule of the analysis target compound.

Examples of the framework-forming aromatic compound include a fused polycyclic aromatic compound. Examples of the fused polycyclic aromatic compound include the compounds respectively represented by the following formulas (5a) to (5i).

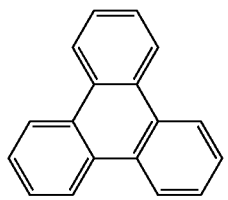

(5a)

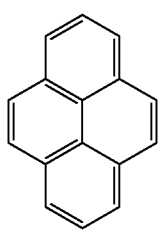

(5b)

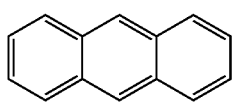

(5c)

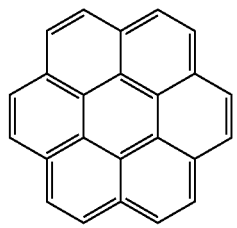

(5d)

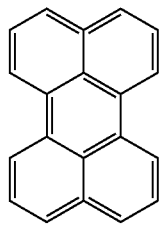

(5e)

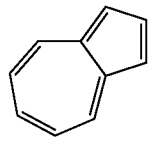

(5f)

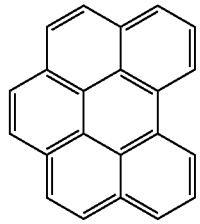

(5g)

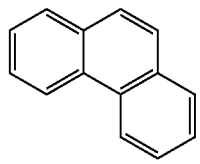

(5h)

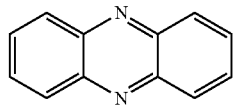

(5i)

These compounds may have a substituent at an arbitrary position of the aromatic ring. Examples of the substituent include an alkyl group such as a methyl group, and an ethyl group; an amino group; a substituted amino group such as a methylamino group, and a dimethylamino group; a hydroxy group; an alkoxy group such as a methoxy group, and an ethoxy group; a mercapto group; an alkylthio group such as a methylthio group, and an ethylthio group; a nitro group; a cyano group; a carboxyl group; and the like.

Examples of the polynuclear metal complex include the compounds listed below.

(1) Compound that includes only a ligand and a metal ion (polynuclear metal complex (α))

(2) Compound that includes the polynuclear metal complex (α) and the framework-forming aromatic compound (polynuclear metal complex (β))

(3) Compound that includes the polynuclear metal complex (α) or the polynuclear metal complex (β), and a guest molecule (e.g., solvent molecule) included therein (polynuclear metal complex (γ))

It is preferable that the polynuclear metal complex used in the invention does not lose crystallinity even after the molecule of the analysis target compound has been introduced into the pores and the voids, and have relatively large pores and voids.

A polynuclear metal complex having such characteristics can be easily obtained by utilizing the tridentate ligand represented by the formula (1).

Examples of the polynuclear metal complex that is obtained by utilizing the tridentate ligand represented by the formula (1) include polynuclear metal complexes respectively represented by the following formulas (6a) to (6c):

$$[(MX_2)_3(L)_2(solv)_a]_b \quad (6a)$$

$$[(MX_2)_3(L)_2(SA)_c(solv)_a]_b \quad (6b)$$

$$[(MX_2)_3(L)_4(solv)_a]_b \quad (6c)$$

wherein M is a divalent ion of a metal that belongs to Groups 8 to 12 in the periodic table, X is a monovalent anionic monodentate ligand, L is the tridentate ligand represented by the formula (1), "solv" is a guest molecule (e.g., solvent molecule) used during synthesis, "SA" is the framework-forming aromatic compound, and a, b, and c are an arbitrary natural number.

Examples of such polynuclear metal complexes include polynuclear metal complexes respectively represented by the following formulas (7a) to (7d):

$$[(ZnI_2)_3(TPT)_2(solv)_a]_b \quad (7a)$$

$$[(ZnBr_2)_3(TPT)_2(solv)_a]_b \quad (7b)$$

$$[(ZnI_2)_3(TPT)_2(SA)_c(solv)_a]_b \quad (7c)$$

$$[(Co(NCS)_2)_3(TPT)_4(solv)_a]_b \quad (7d)$$

wherein "solv", "SA", a, b, and c are the same as defined above.

Examples of the polynuclear metal complex represented by the formula (7a) include $[(ZnI_2)_3(TPT)_2(PhNO_2)_{5.5}]_n$ (polynuclear metal complex 1) disclosed in JP-A-2008-214584 and J. Am. Chem. Soc. 2004, v. 126, pp. 16292-16293, and a polynuclear metal complex obtained by replacing all or some of the reaction solvent molecules included in the polynuclear metal complex 1 with a replacement solvent.

Examples of the polynuclear metal complex represented by the formula (7b) include $[(ZnBr_2)_3(TPT)_2(PhNO_2)_5(H_2O)]_n$ (polynuclear metal complex 2) disclosed in JP-A-2008-214318, and a polynuclear metal complex obtained by replacing all or some of the reaction solvent molecules included in the polynuclear metal complex 2 with a replacement solvent.

Examples of the polynuclear metal complex represented by the formula (7c) include $[(ZnI_2)_3(TPT)_2(TPH)(PhNO_2)_{3.9}(MeOH)_{1.8}]_n$ (polynuclear metal complex 3) and $[(ZnI_2)_3(TPT)_2(PER)(PhNO_2)_4]_n$ (polynuclear metal complex 4) disclosed in JP-A-2006-188560, and a polynuclear metal complex obtained by replacing all or some of the reaction solvent molecules included in the polynuclear metal complex 3 or 4 with a replacement solvent.

Examples of the polynuclear metal complex represented by the formula (7d) include $[(Co(NCS)_2)_3(TPT)_4(DCB)_{25}(MeOH)_5]_n$ (polynuclear metal complex 5) disclosed in WO2011/062260, and a polynuclear metal complex obtained by replacing all or some of the reaction solvent molecules included in the polynuclear metal complex 5 with a replacement solvent.

A known polynuclear metal complex that is referred to as "porous coordination polymer (PCP)" or "metal-organic framework (MOF)" may also be used as the polynuclear metal complex instead of the polynuclear metal complexes respectively represented by the formulas (6a) to (6c). For example, Material Matters No. 7—Fundamentals of Porous Coordination Polymers (PCP)/Metal-Organic Frameworks (MOF) (September, 2012) published by Sigma-Aldrich lists polynuclear metal complexes such as $[Cu_2(bzdc)_2(pyz)]_n$
(wherein "bzdc" is 2,3-pyrazinedicarboxylic acid, "pyz" is pyrazine, and n is an arbitrary number), $[Zn_2(14bdc)_2(dabco)]_n$
(wherein "14bdc" is 1,4-benzenedicarboxylic acid, "dabco" is 1,4-diazabicyclo[2.2.2]octane, and n is an arbitrary number), $[Cu(dhbpc)_2(bpy)]_n$
(wherein "H$_3$dhbpc" is 4,4'-dihydroxybiphenyl-3-carboxylic acid, "bpy" is 4,4'-bipyridyl, and n is an arbitrary number), and $[Cr(btc)_2]_n$
(wherein "H$_3$btc" is 1,3,5-benzenetricarboxylic acid, and n is an arbitrary number). The invention may be used for a method of determination when these single crystals are used as crystalline sponges.

The polynuclear metal complex may be synthesized by an arbitrary method without limitation, using a known method.

For example, Material Matters No. 7—Fundamentals of Porous Coordination Polymers (PCP)/Metal-Organic Frameworks (MOF) (September, 2012) published by Sigma-Aldrich describes a solution method that mixes a solution that includes a multidentate ligand and the like with a solution that includes a metal ion and the like;

a hydrothermal method that charges a pressure-resistant vessel with a solvent, a multidentate ligand, a metal ion, and the like, seals the pressure-resistant vessel, and heats the mixture to a temperature equal to or higher than the boiling point of the solvent to effect a hydrothermal reaction;

a microwave method that charges a vessel with a solvent, a multidentate ligand, a metal ion, and the like, and applies microwaves to the mixture;

an ultrasonic method that charges a vessel with a solvent, a multidentate ligand, a metal ion, and the like, and applies ultrasonic waves to the mixture;

a solid-state synthesis method that mechanically mixes a multidentate ligand, a metal ion, and the like without using a solvent; and the like. A single crystal of the polynuclear metal complex can be obtained using these methods.

It is preferable to use the solution method since it is unnecessary to use special equipment.

For example, a solution prepared by dissolving a metal ion-containing compound in a second solvent is added to a solution prepared by dissolving a multidentate ligand in a first solvent, and the mixture is allowed to stand at 0 to 70° C. for several hours to several days.

The metal ion-containing compound is not particularly limited. Examples of the metal ion-containing compound include a compound represented by $MX_n$. Note that M is a metal ion, X is a counter ion, and n is the valence of M.

Specific examples of X include $F^-$, $Cl^-$, $Br^-$, $I^-$, $SCN^-$, $NO_3^-$, $ClO_4^-$, $BF_4^-$, $SbF_4^-$, $PF_6^-$, $AsF_6^-$, $CH_3CO_2^-$, and the like.

Examples of the reaction solvent (first solvent and second solvent) include an aromatic hydrocarbon such as benzene, toluene, xylene, chlorobenzene, 1,2-dichlorobenzene, and nitrobenzene; an aliphatic hydrocarbon such as n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide (DMSO); an amide such as N,N-dimethylformamide and N-methylpyrrolidone; an ether such as diethyl ether, tetrahydrofuran, 1,2-dimethoxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

When it is desired to obtain a relatively large single crystal of the polynuclear metal complex, it is preferable that the first solvent and the second solvent be immiscible with each other (i.e., separated into two layers). For example, nitrobenzene, dichlorobenzene, a mixed solvent including nitrobenzene and methanol, or a mixed solvent including dichlorobenzene and methanol may be used as the first solvent, and methanol may be used as the second solvent.

The polynuclear metal complexes 1 to 5 can be synthesized in accordance with the methods described in the above literature.

Shapes of the single crystal of the invention are not particularly limited. Examples of the single crystal include crystals in the shape of a quadrangular prism such as a triangular prism, a quadrangular prism, a hexagonal column, and the like, and crystals in the shape of a round column.

The size of one side of one single crystal of the invention is normally 10 to 2000 μm, and preferably 60 to 200 μm.

The single crystal of the invention is characterized in that the single crystal maintains single crystallinity even after bringing the single crystal into contact with a solvent which is chemically identical to the solvent of the analysis target compound-containing solution. Such a single crystal is preferred as a single crystal used for producing a crystal structure analysis sample.

In the present invention, "single crystallinity" refers to a property of giving a spot of diffracted X-rays or neutron which is sufficient to allow crystal structure analysis when a sample is irradiated with X-rays or neutron.

A method for determination of "single crystallinity" is not particularly limited. Examples of the method include following methods:
(i) A method including observing a crystal with a microscope, and determining that the crystal has lost single crystallinity when the crystal has crack as a whole, or has impaired transparency. That is, when a crystal is observed with a microscope, the crystal that does not have cracks, breakage, and the like as a whole, and has transparency can be determined as maintaining single crystallinity.

In this case, the method for determination of whether a crystal maintains single crystallinity is preferably crossed Nicols observation using a polarization microscope which facilitates the determination. A crystal without color irregularities or brightness irregularities, when observed using crossed Nicols, can be determined as maintaining single crystallinity.

Figure 11:
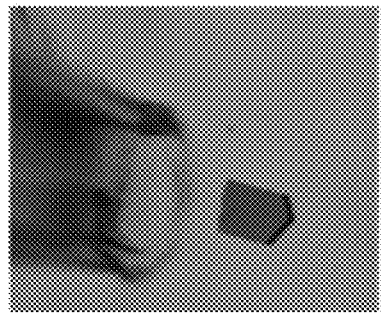
FIG. 11 shows photographic images derived from observation of a crystal before and after the measurement of shape retention ratio (2) of Case 3 in Example 14.
Figure 11:
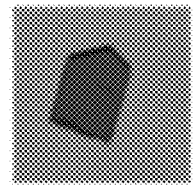

Note that, when a crystal is observed using a microscope, the crystal can be impaired by dehydration. When the deterioration can occur, the crystal is preferably immersed in a solvent during the observation of the crystal.
(ii) A method including determining that a single crystal has single crystallinity when the rate of change in absorbance of UV-vis absorption spectrum of the single crystal within the wavelength range of 450 to 500 nm is 10% or less between before and after bringing the single crystal into contact with a solvent which is chemically identical to a solvent of an analysis target compound-containing solution. As shown in FIG. 11, for example, when UV-vis absorption spectrum of a single crystal is measured, in a crystal having single crystallinity, change in absorbance within the wavelength range of 450 to 500 nm is small between before and after bringing the crystal into contact with a solvent which is chemically identical to a solvent of an analysis target compound-containing solution. On the other hand, in a crystal without single crystallinity, absorbance within the wavelength range of 450 to 500 nm is increased after bringing the crystal into contact with a solvent which is chemically identical to a solvent of an analysis target compound-containing solution, that is, the absorbance changes significantly.

Generally, when UV-vis absorption spectrum of a metal complex crystal specimen maintaining single crystallinity is measured, an absorption band is observed within the wavelength range of 1000 nm or less.

On the other hand, in a specimen which has lost single crystallinity (i.e., single crystallinity has been lost such that the specimen is not suitable for use in the crystalline sponge method), absorbance is significantly increased within the wavelength range of 450 to 700 nm. This tendency of increasing absorbance is remarkable within the wavelength range of 450 to 500 nm.

Loss of single crystallinity deprives the single crystal of permeability within a broad range of wavelengths, and thus a baseline of an absorption spectrum is raised from a baseline level of a single crystal. This tendency is also observed in an analysis of a powder sample (of an organic compound/metal complex) which does not have single crystallinity basically.

For example, a complex crystal maintaining single crystallinity used in Example [1] exhibit orange color, which corresponds to showing significant absorption characteristics around 350 nm. On the other hand, when the complex loses single crystallinity, the orange color gradually fades and the complex turns greenish color. Consequently, the absorption band is broadened toward longer wavelength, and then increase in absorbance at the wavelength range of 450 nm or more is observed.

According to the determination procedure described above, it is possible to determine objectively whether a crystal maintains single crystallinity.

A solvent of an analysis target compound-containing solution used is appropriately selected from solvents which do not dissolve a single crystal used and dissolve an analysis target compound. Then, a solvent preselected from the viewpoint above is brought into contact with a single crystal. Specific examples of a solvent of a solution containing an analysis target compound are shown in a section of a method for producing a crystal structure analysis sample.

A method for bringing a single crystal into contact with a solvent is not particularly limited. Since efficient contact between the two materials can be achieved, a method including immersing a single crystal in a solvent is preferred.

A time duration of contact between the two materials is normally, but not particularly limited to, 1 to 7 days, and preferably 6 to 7 days. In addition, the time duration of contact described above is preferably longer than a time duration of contact between a single crystal and an analysis target compound-containing solution producing a crystal structure analysis sample.

A temperature at the time of the contact is preferably, but not particularly limited to, comparable to the temperature of a solution when the single crystal is brought into contact with the analysis target compound-containing solution. The temperature at the time of the contact is normally 0 to 100° C., and preferably 4 to 50° C.

(iii) A method including determining that a single crystal has single crystallinity when shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in a solvent which is chemically identical to a solvent of an analysis target compound-containing solution at a liquid depth of 5 mm.

Semiempirically, when a single crystal is subjected to the operation described above, most single crystals which do not maintain their shape cannot be used as single crystals for a crystal structure analysis sample. Thus, the phenomenon is defined as a method.

(iv) When shape retention ratio of the single crystal is 90% or more between before and after an operation of sucking a solution containing the single crystal and a solvent which is chemically identical to the solvent of the analysis target compound-containing solution at a suction rate of 6 μL/sec using a pipet tip for 20 to 200 μL having an aperture of 250 μm in diameter at a liquid depth of 5 mm, and then discharging the solution containing the single crystal at a discharge rate of 6 μL/sec, and then a single crystal is subjected to the operation described above, most single crystals which do not maintain their shape cannot be used as single crystals for a crystal structure analysis sample. Thus, the phenomenon is defined as a method.

The single crystal of the invention is suitable for producing a crystal structure analysis sample, and there is a high probability of success in analyzing molecular structure of an analysis target compound with the crystal structure analysis sample.

2) Method for Determination of Whether Single Crystal is Good or Bad

Embodiment 2 of the invention is a method for determination of whether a single crystal used for producing a crystal structure analysis sample of an analysis target compound is good or bad by bringing the porous compound single crystal having a three-dimensional framework, and having pores and/or voids, which are defined by the three-dimensional framework, that are three-dimensionally arranged in an ordered manner into contact with an analysis target compound-containing solution to arrange molecules of the analysis target compound in the pores and/or the voids in an ordered manner, comprising step (A1): bringing the single crystal into contact with a solvent which is chemically identical to the solvent of the analysis target compound-containing solution; and step (A2): when the single crystal is confirmed to maintain single crystallinity even after the contact of the single crystal with the solvent in step (A1), determining the single crystal as suitable for producing the crystal structure analysis sample.

The single crystal used in step (A1) can produce the crystal structure analysis sample of the analysis target compound by introducing the analysis target compound into pores and/or the voids contained in the single crystal to arrange the compound in an ordered manner.

For example, when a single crystal of a polynuclear metal complex is used as the single crystal, a relatively large single crystal [e.g., a major axis (longest axis) is about 200 μm, and the minor axis (shortest axis) is about 100 μm] can be selected from single crystals of a polynuclear metal complex produced, and then a single crystal without edge or crack breakage and having superior transparency can be appropriately selected by visual observation, or a single crystal without brightness irregularities or transparency irregularities can be appropriately selected by crossed Nicols observation using a polarization microscope, and then the selected single crystal can be used in step (A1).

The solvent which is brought into contact with the single crystal in step (A1) is a solvent which is chemically identical to the solvent of the analysis target compound-containing solution. Thus, in the invention, after step (A1), the analysis target compound can be dissolved in the solvent itself used in step (A1) to prepare the analysis target compound-containing solution, or the analysis target compound can be dissolved in a solvent which is the same chemical substance as the solvent used in step (A1) but is not the solvent itself used in step (A1) to prepare the analysis target compound-containing solution.

In the method of the invention, a solvent of an analysis target compound-containing solution, a method for bringing a single crystal into contact with a solvent, a time duration of contact between the two materials, a temperature at the time of the contact, and the like is the same as the contents in the section of the single crystal of the invention described above.

Further, specific examples of the methods for determination of single crystallinity is also the same as the contents in the section of the single crystal of the invention described above.

According to the method for determination of the invention, a single crystal suitable for producing a crystal structure analysis sample can be screened, and there is a high probability of success in analyzing the molecular structure of an analysis target compound.

3) Method for Preparing Analysis Target Compound-Containing Solution

Embodiment 3 of the invention is a method for preparing an analysis target compound-containing solution used for producing a crystal structure analysis sample of the analysis target compound by bringing a porous compound single crystal having a three-dimensional framework, and having pores and/or voids, which are defined by the three-dimensional framework, that are three-dimensionally arranged in an ordered manner into contact with the analysis target compound-containing solution to arrange molecules of the analysis target compound in the pores and/or the voids in an ordered manner, the method comprising step (B1): bringing the single crystal into contact with a solvent dissolving the analysis target compound, and step (B2): when the single crystal is confirmed to maintain single crystallinity even after the contact of the single crystal with the solvent in step (B1), determining the solvent as suitable for a solvent of the analysis target compound-containing solution used for producing the crystal structure analysis sample.

The method determines a suitable solvent used for preparing an analysis target compound-containing solution.

A solvent used for preparing an analysis target compound-containing solution should fulfil a requirement of (a) solubilizing an organic compound which is a target for analysis, and a single crystal used should fulfil a requirement of (b) maintaining single crystallinity even in the solvent.

With respect to the requirement for the solvent of (a) solubilizing an organic compound which is a target for an analysis, it is relatively easy to select a suitable solvent semiempirically. On the other hand, with respect to the requirement for a single crystal used of (b) maintaining single crystallinity even in a solvent, most crystals cannot be identified as fulfilling the requirement without actually producing a crystal structure analysis sample and carrying out a crystal structure analysis. However, according to the invention, by carrying out a defined method for determination before producing a crystal structure analysis sample, a solvent used for an analysis target compound-containing solution can be selected.

A solvent which can be used as a solvent of an analysis target compound-containing solution refers to the solvent which fulfils two requirements of (1) being unable to dissolve a single crystal used, and (2) dissolving an analysis target compound. Hereinafter, the solvent is sometimes called as "candidate solvent".

The method for preparation of present invention include analyzing whether a candidate solvent is hard to make a single crystal lose single crystallinity, determining a solvent used for producing a crystal structure analysis sample based on the knowledge obtained above, and then preparing an analysis target compound-containing solution using the determined solvent.

That is, the invention of "a method for determination of whether a single crystal is good or bad" described above is a method for distinguishing a crystal maintaining single crystallinity even after bringing the crystal into contact with an analysis target compound when a solvent, which is used as a solvent of a solution of the analysis target compound, is already determined for a reason of solubility of the analysis target compound and the like, whereas the invention is a method, when there are various candidate solvents, for finding a solvent, which is hard to make a single crystal lose single crystallinity, from the candidate solvents, and preparing an analysis target compound-containing solution using the solvent.

Although there is a difference in objects, which are a single crystal and a solvent, that is a target of attention, basically the same operation is carried out in the present invention and the invention of "a method for determination of whether a single crystal is good or bad".

Thus, "a porous compound single crystal" used in the present invention can be the same as that described in the invention of "a method for determination of whether a single crystal is good or bad". In addition, a method for bringing a single crystal into contacting with a solvent, conditions (temperature, and duration of time) of contact, and the method for determination of "single crystallinity" used in the present invention can be the same as those described in the invention of "a method for determination of whether a single crystal is good or bad".

A solution containing an analysis target compound prepared according to the method of the invention is hard to make a single crystal lose single crystallinity. Thus, a crystal structure analysis sample of good quality can be produced more reliably by utilizing the solution.

4) Method for Producing Crystal Structure Analysis Sample

Embodiment 4 of the invention is (I) a method for producing a crystal structure analysis sample, the method comprising bringing the single crystal of the invention into contact with an analysis target compound-containing solution to arrange molecules of the analysis target compound in the pores and/or the voids in an ordered manner, or (II) a method for producing a crystal structure analysis sample, the method comprising bringing the single crystal, which is confirmed to maintain single crystallinity by the method for determination of whether the single crystal is good or bad according to the invention, into contact with an analysis target compound-containing solution to arrange molecules of the analysis target compound in the pores and/or the voids in an ordered manner.

The size of an analysis target compound is not particularly limited as long as the analysis target compound can enter pores and/or voids of a single crystal. The molecular weight of the analysis target compound is normally 20 to 3,000, and preferably 100 to 2,000.

It is also preferable to roughly determine the molecular size of the analysis target compound in advance by nuclear magnetic resonance spectroscopy, mass spectrometry, elemental analysis, or the like, and appropriately select a single crystal having appropriate pores and voids.

The single crystal may be brought into contact with the analysis target compound-containing solution in an arbitrary way. For example, the single crystal may be brought into contact with the analysis target compound-containing solution using a method that immerses the single crystal in the analysis target compound-containing solution, or a method that charges a capillary with the single crystal, and passes the analysis target compound-containing solution through the capillary.

A solvent of an analysis target compound-containing solution is appropriately selected from solvents which do not dissolve a single crystal used and dissolve an analysis target compound as described above.

Specific examples of the solvent include an aromatic hydrocarbon such as benzene, toluene, xylene, chlorobenzene, 1,2-dichlorobenzene, and nitrobenzene; an aliphatic hydrocarbon such as n-butane, n-pentane, n-hexane, and n-heptane; an alicyclic hydrocarbon such as cyclopentane, cyclohexane, and cycloheptane; a nitrile such as acetonitrile and benzonitrile; a sulfoxide such as dimethyl sulfoxide (DMSO); an amide such as N,N-dimethylformamide and N-methylpyrrolidone; an ether such as diethyl ether, tetrahydrofuran, 1,2-dimethoxyethane, and 1,4-dioxane; an alcohol such as methanol, ethanol, and isopropyl alcohol; a ketone such as acetone, methyl ethyl ketone, and cyclohexanone; a cellosolve such as ethylcellosolve; a halogenated hydrocarbon such as dichloromethane, chloroform, carbon tetrachloride, and 1,2-dichloroethane; an ester such as methyl acetate, ethyl acetate, ethyl lactate, and ethyl propionate; water; and the like. These solvents may be used either alone or in combination.

An analysis target compound-containing solution is preferably prepared by the method for preparation of the invention as described above.

An amount of an analysis target compound contained in an analysis target compound-containing solution is normally, but not particularly limited to, 5 ng to 1 g, and preferably 5 ng to 50 µg.

According to the method of the invention, even when the amount of an analysis target compound is very small, a crystal structure analysis sample of good quality can be produced more reliably.

A time duration of contact between a single crystal and an analysis target compound-containing solution is normally, but not particularly limited to, 1 hour to 2 weeks, and preferably 1 to 2 days.

A temperature at the time of bringing a single crystal into contact with an analysis target compound-containing solution is normally, but not particularly limited to, 0 to 100° C., and preferably 4 to 50° C.

The crystal structure analysis sample obtained by a method of the invention has a configuration in which the molecules of an analysis target compound are arranged in the pores and/or the voids of the porous compound single crystal in an ordered manner.

The expression "the molecules of an analysis target compound are arranged in an ordered manner" used herein means that the molecules of an analysis target compound are included in the pores and the voids of the single crystal in an ordered manner to such an extent that the structure of the compound can be determined by crystal structure analysis.

It is preferable that the crystal structure analysis sample be designed so that the molecular structure can be determined with a resolution of at least 1.5 Å by applying MoKα radiation (wavelength: 0.71 Å) generated at a tube voltage of 24 kV and a tube current of 50 mA to the crystal structure analysis sample, and detecting the diffracted X-rays using a CCD detector.

The crystal structure analysis sample need not necessarily be designed so that the molecules of an analysis target compound are included in all of the pores and the voids of the porous compound single crystal as long as the molecular structure of the analysis target compound can be determined. For example, the solvent used to prepare the analysis target compound-containing solution may be included in some of the pores and the voids of the single crystal.

It is preferable that the occupancy ratio of the molecules of an analysis target compound in the crystal structure analysis sample is 10% or more.

The term "occupancy ratio" used herein in connection with the molecules of an analysis target compound refers to a value obtained by crystal structure analysis, and represents the amount of guest molecules actually present in the single crystal with respect to the amount (=100%) of guest molecules (i.e., the molecules of an analysis target compound) in an ideal inclusion state.

As described above, a method for producing a crystal structure analysis sample according to the invention uses a single crystal which is confirmed to maintain single crystallinity by the method described above. Thus, a crystal structure analysis sample of good quality ca be produced more reliably according to the method of the invention.

5) Method for Determining Molecular Structure of Analysis Target Compound

Embodiment 5 of the invention is a method for determining a molecular structure of an analysis target compound comprising performing crystal structure analysis using a method for producing a crystal structure analysis sample according to the invention.

In the invention, a crystal structure analysis sample can be produced by using a single crystal of the invention or a single crystal which is determined as good by a method for determination of whether a single crystal is good or bad according to the invention, and using a solution of an analysis target compound prepared by a method for preparing a solution according to the invention.

The method for determining a molecular structure according to the invention may utilize any of X-ray diffraction or neutron diffraction.

When the molecular structure of an analysis target compound is determined by a method of the invention, the determination can be performed in a similar manner to a conventional method, except that a crystal structure analysis sample obtained by the method as described above is mounted instead of a single crystal as in the conventional method.

EXAMPLES

The invention is further described below by way of examples. Note that the invention is not limited to the following examples.

[Microscopic Observation]

In microscopic observation of a single crystal which had been brought into contact with a solvent, whether single crystallinity of the single crystal was maintained or not was determined according to criteria provided below.

A: The single crystal has no crack.

B: The single crystal has some cracks

C: The single crystal has cracks as a whole; or the single crystal loses transparency as a whole.

Then, when the crystal is classified as Grade A or Grade B, a crystal structure analysis sample of good quality can be produced. On the other hand, when the expression "retention ratio" refers to the ratio of the number of crystals of Grade A and Grade B relative to the number of single crystals which has been brought into contact with a solvent, when the retention ratio is 1% or more, the solvent can be determined as usable for a solvent of an analysis target compound-containing solution.

[UV-Vis Absorption Spectrum]

Ultraviolet-visible optical absorption spectra of a single crystal before and after bringing the single crystal into contact with a solvent was measured as follows.

In a quartz cell (manufactured by GL SCIENCES INC.) of 1 cm×1 mm (optical path length=1 mm), single crystals were dispersed in an appropriate organic solvent which does not have a characteristic interfering absorption within a wavelength range in which observation was carried out (preferably a solvent which is chemically identical to the solvent with which the single crystal was brought into contact as described above), and then measurement was carried out by placing the quartz cell in the test chamber of a UV-vis absorption spectrometer (UV-3150, manufactured by SHIMADZU CORPORATION).

[Measurement of Shape Retention Ratio (1) of Single Crystal]

Shape retention ratio (1) of a single crystal was determined as follows.

A tungsten steel needle for manipulating the crystal (needle diameter=0.1 mm) having a needle diameter of 0.1 mm was brought into contact with a single crystal, and the single crystal was subjected to 10 mm shift by exerting a force of $10^{-2}$ N or less. Specifically, using a tungsten steel needle for manipulating the crystal (manufactured by HAMPTON RESEARCH CORP., needle diameter=0.1 mm), the single crystal was maintained in a petri dish under the condition that the single crystal was immersed in a solvent, the single crystal was subjected to 10 mm parallel shift by exerting a force of $10^{-2}$ N or less (preferably $10^{-5}$ to $10^{-2}$ N) at a liquid depth of 5 mm. The shifted single crystal was checked by optical microscopic observation, and the image of the single crystal was overlaid on the image obtained before the shift, and then a percentage of shape of the single crystal retained was calculated to obtain "shape retention ratio (1)".

More specifically, shapes of the crystal before and after the shift can be compared by using various commercially available software to calculate shape retention ratio (1). More primitively, photographic images of the crystal taken before and after the shift at the same magnification can be printed, and then ratios of areas of the crystal can be compared (by weighing the pieces of paper) to calculate shape retention ratio (1).

[Measurement of Shape Retention Ratio (2) of Single Crystal]

Shape retention ratio (2) of a single crystal was determined as follows.

Suction was performed at a suction rate of 6 μL/sec using a micropipet having an aperture (liquid suction hole) of 250 μm in diameter. Specifically, a single crystal was maintained in a petri dish under the condition that the single crystal was immersed in a solvent, and then, the single crystal was subjected to a suction operation in the liquid at a liquid depth of 5 mm using a Nichipet EX Plus II (manufactured by NICHIRYO CO., LTD.) and a pipet tip (manufactured by AS ONE Corporation, Friend Tips for 20 to 200 μL, aperture of 250 μm in diameter). The suction rate of the crystal was set to suck at 6 μL/sec. The sucked crystal was gradually released (at a release rate of 6 μL/sec) in the petri dish again, and then the single crystal was checked by optical microscopic observation, and the image of the single crystal was overlaid on the image obtained before the shift, and then a percentage of shape of the single crystal retained was calculated to obtain "shape retention ratio (2)".

Example 1

A crystal of a porous complex 1 was synthesized according to a method described in a literature (Aust. J. Chem. 2013, 66, 452-463) in a test tube using 2,4,6-tris(4-pyridyl)-1,3,5-triazine as a ligand, cobalt thiocyanate as a source of metal, and a mixed solvent including 1,1,2,2-tetrachloroethane (TCE) and ethanol as a solvent.

The crystals of the porous complex 1 deposited on an inner wall of the test tube were scraped off with a spatula so that the crystals were collected at the bottom of the test tube, and then the solvents were removed. Then, after the addition of another TCE, the mixture was allowed to stand for 3 hours. Then, the whole mixture was transferred to a petri dish, and then about 100 crystals of good shape were picked up to be immersed in 4 mL of TCE together with small amount of the mother liquor. The immersed crystals were allowed to stand at 25° C. for 1 week, and then the crystals were observed with a microscope.

Figure 2:
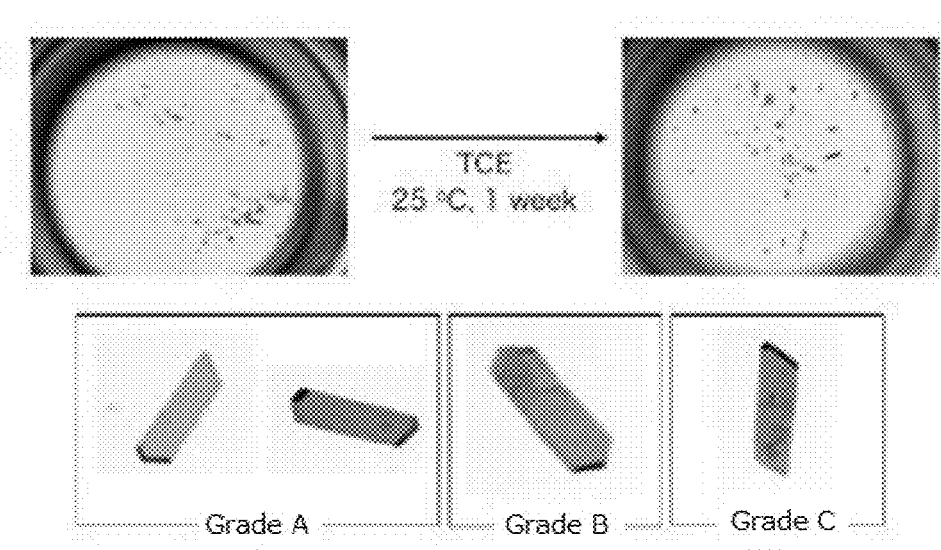
FIG. 2 shows photographic images of crystals evaluated as Grade A, B, and C in Example 1.
Figure 3:
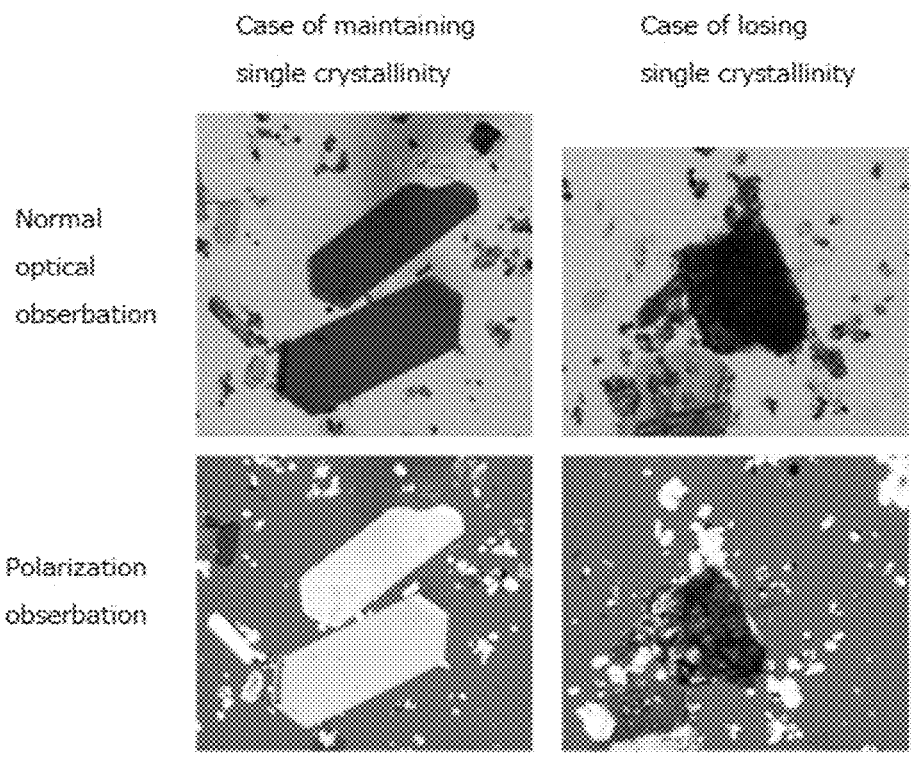
FIG. 3 shows photographic images derived from observation using a polarization microscope in Example 1.

Table 1 shows the results derived from the observation. Further, photographic images taken concurrent with the observation are shown in FIG. 2. Furthermore, photographic images obtained by observation with a polarization microscope are shown in FIG. 3.

Example 2

Crystals were brought into contact with a solvent, and then the crystals were observed with a microscope in a similar manner to Example 1, except that cyclohexane was used instead of TCE as a solvent used for allowing the immersed crystals to stand at 25° C. for 1 week.

Table 1 shows the results derived from the observation.

Example 3

Crystals were brought into contact with a solvent, and then the crystals were observed with a microscope in a similar manner to Example 1, except that toluene was used instead of TCE as a solvent used for allowing the immersed crystals to stand at 25° C. for 1 week.

Table 1 shows the results derived from the observation.

Example 4

Crystals were brought into contact with a solvent, and then the crystals were observed with a microscope in a similar manner to Example 1, except that ethyl acetate was used instead of TCE as a solvent used for allowing the immersed crystals to stand at 25° C. for 1 week.

Table 1 shows the results derived from the observation.

Comparative Example 1

Crystals were brought into contact with a solvent, and then the crystals were observed with a microscope in a similar manner to Example 1, except that the immersed crystals were allowed to stand in methanol at 25° C. for 5 minutes instead of in TCE at 25° C. for 1 week.

In this case, all crystals were impaired to the extent that the crystals did not retain original shapes within 5 minutes, and none of crystals of Grades A to C was observed.

Table 1 shows the results derived from the observation. The results show that TCE, cyclohexane, toluene, and ethyl acetate are preferable as a solvent of a solution.

TABLE 1

| | | Solvent | Number of single crystals immersed | Number of single crystals of Grade A | Number of single crystals of Grade B | Number of single crystals of Grade C | Retention ratio (%) |
|---|---|---|---|---|---|---|---|
| Example | 1 | 1,1,2,2-Tetrachloroethane | 111 | 86 | 12 | 13 | 88 |
| | 2 | Cyclohexane | 108 | 56 | 11 | 41 | 62 |
| | 3 | Toluene | 100 | 52 | 3 | 45 | 55 |
| | 4 | Ethyl acetate | 101 | 22 | 10 | 69 | 32 |
| Comparative Example | 1 | Methanol | 100 | 0 | 0 | 0 | 0 |

[Measurement of UV-Vis Absorption Spectrum]

Ultraviolet-visible optical absorption spectra of a single crystal before and after bringing a porous complex 1 into contact with a solvent were measured. Ultraviolet-visible optical absorption spectra are shown in FIG. 4.

Figure 4:
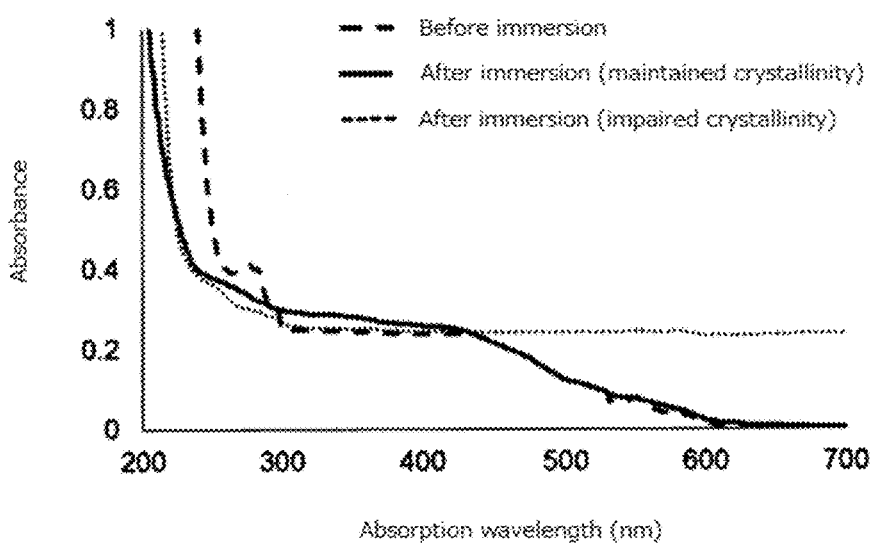
FIG. 4 shows ultraviolet-visible optical absorption spectra of a single crystal before and after bringing a porous complex 1 into contact with a solvent.

In FIG. 4, "before immersion" refers to an ultraviolet-visible optical absorption spectrum of the single crystal before immersing the porous complex 1 in the solvent, "after immersion (maintained crystallinity)" refers to an ultraviolet-visible optical absorption spectrum of the single crystal of Grade A as described above, and "after immersion (impaired crystallinity)" refers to an ultraviolet-visible optical absorption spectrum of the single crystal of the porous complex 1 of Grade C as described above.

Example 5

Figure 5:
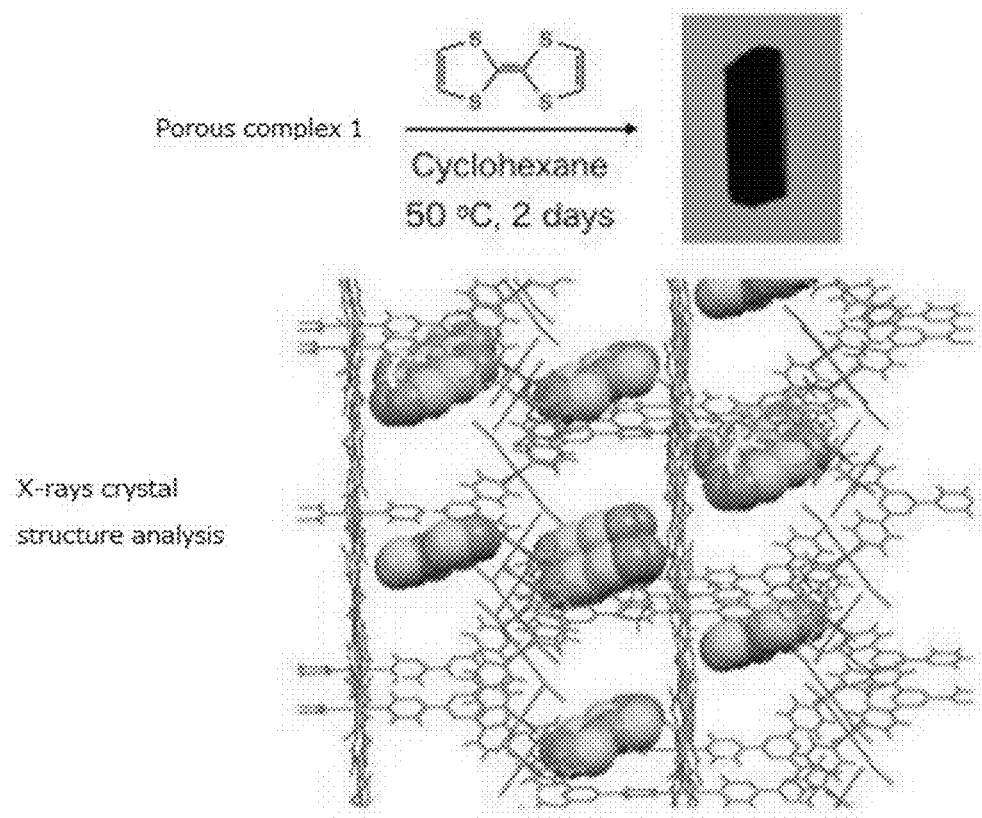
FIG. 5 shows a photographic image of a crystal (upper), and a result of crystal structure analysis (lower) obtained in Example 5.

A crystal judged as Grade A in Example 2 was immersed in a solution of tetrathiafulvalene in cyclohexane at 50° C. for 2 hours. The resultant crystal structure analysis sample was used for performing crystal structure analysis. The results are shown in Table 2 and FIG. 5.

TABLE 2

| Crystal system | Monoclinic |
|---|---|
| Space groups | P2/c |
| a (Å) | 24.438 |
| b (Å) | 22.614 |
| c (Å) | 25.772 |
| α (°) | 90 |
| β (°) | 105.28 |
| γ (°) | 90 |
| Z | 8 |
| R1 (%) | 21.15 |

Example 6

A crystal judged as Grade A in Example 1 was immersed in a solution of bis(p-methoxyphenyl)diphenylmethane in TCE at 50° C. for 1 day. The resultant crystal structure analysis sample was used for performing crystal structure analysis. The results are shown in Table 3.

TABLE 3

| Crystal system | Monoclinic |
|---|---|
| Space groups | P2/c |
| a (Å) | 24.336 |
| b (Å) | 22.727 |
| c (Å) | 25.533 |
| α (°) | 90 |
| β (°) | 105.222 |
| γ (°) | 90 |
| Z | 8 |
| R (%) | 28.18 |

Comparative Example 2

A crystal judged as Grade C in Example 1 was immersed in a solution of tetrathiafulvalene in cyclohexane at 50° C. for 2 hours. The resultant a crystal structure analysis sample was used for an attempt to perform crystal structure analysis. However, no spot of diffraction was obtained, and thus crystal structure analysis did not succeed.

Example 7

A porous complex 2 was synthesized according to a method described in a literature (Chem. Asian. J. 2010, 5, 2358-2368) in a test tube using 2,4,6-tris(4-pyridylcarbonyloxy)-1,3,5-benzene as a ligand, copper(I) bromide as a source of metal, a mixed solvent including chloroform and acetonitrile as a solvent.

The crystals of the porous complex 2 deposited on an inner wall of the test tube were scraped off with a spatula so that the crystals were collected at the bottom of the test tube, and then solvents were removed. Then, after the addition of another chloroform, the mixture was allowed to stand for 1 day. Then, the whole mixture was transferred to a petri dish, and then crystals of good shape were picked up to be immersed in 4 mL of chloroform together with small amount of the mother liquor. The immersed crystals were allowed to stand at 25° C. for 1 week, and then the crystals were observed with a microscope.

Figure 6:
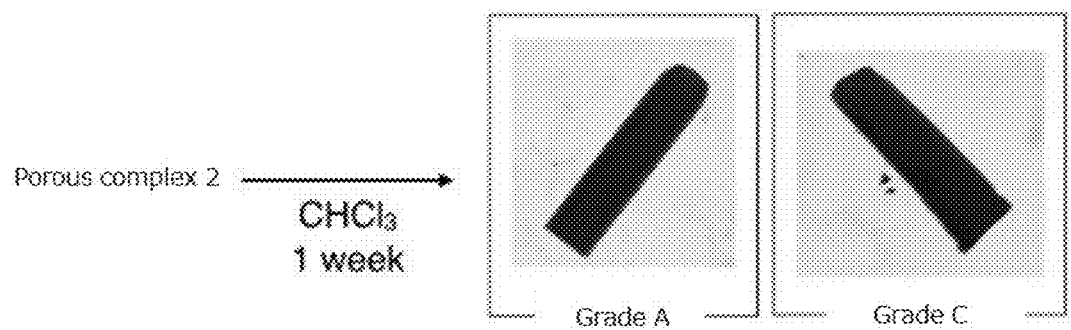
FIG. 6 shows photographic images derived from observation of a crystal obtained in Example 6.
Figure 7:
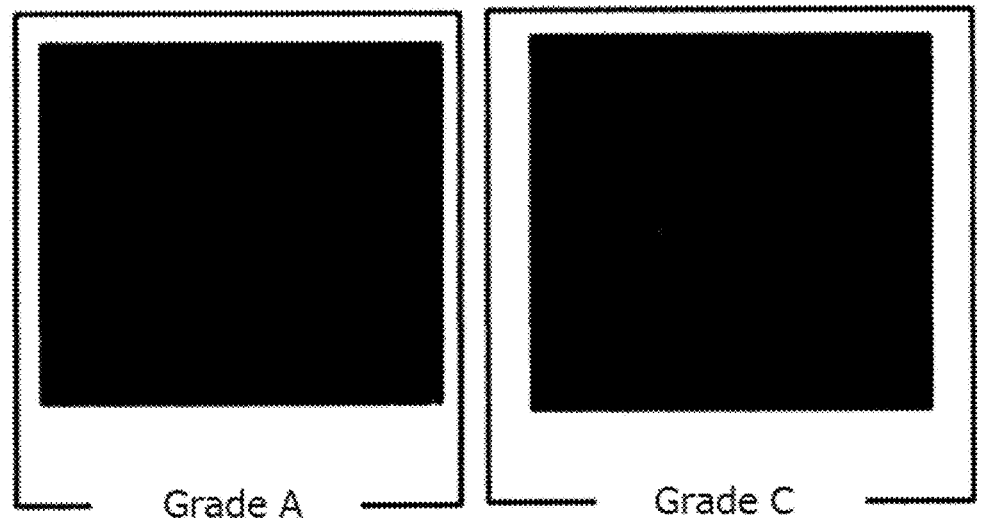
FIG. 7 shows photographic images derived from observation using a polarization microscope in Example 6.

Table 4 shows the results derived from the observation. Further, photographic images taken concurrent with the observation are shown in FIG. 6. Furthermore, photographic images obtained by observation with a polarization microscope are shown in FIG. 7.

Example 8

Crystals were brought into contact with a solvent, and then the crystals were observed with a polarization microscope in a similar manner to Example 7, except that cyclohexane was used instead of chloroform as a solvent used for allowing the immersed crystals to stand at 25° C. for 1 week.

Table 4 shows the results derived from the observation.

Example 9

Crystals were brought into contact with a solvent, and then the crystals were observed with a polarization microscope in a similar manner to Example 7, except that nitromethane was used instead of chloroform as a solvent used for allowing the immersed crystals to stand at 25° C. for 1 week.

Table 4 shows the results derived from the observation.

Example 10

Crystals were brought into contact with a solvent, and then the crystals were observed with a polarization microscope in a similar manner to Example 7, except that 1,2-dimethoxyethane was used instead of chloroform as a solvent used for allowing the immersed crystals to stand at 25° C. for 1 week.

Table 4 shows the results derived from the observation.

Example 11

Crystals were brought into contact with a solvent, and then the crystals were observed with a polarization microscope in a similar manner to Example 6, except that ethyl acetate was used instead of chloroform as a solvent used for allowing the immersed crystals to stand at 25° C. for 1 week.

Table 4 shows the results derived from the observation.

TABLE 4

| | | Solvent | Number of single crystals immersed | Number of single crystals of Grade A | Number of single crystals of Grade B | Number of single crystals of Grade C | Retention ratio (%) |
|---|---|---|---|---|---|---|---|
| Example | 1 | Chloroform | 20 | 14 | 0 | 6 | 95 |
| | 2 | Cyclohexane | 20 | 17 | 0 | 3 | 85 |
| | 3 | Nitromethane | 20 | 12 | 0 | 8 | 60 |
| | 4 | 1,2-Dimethoxyethane | 20 | 9 | 0 | 11 | 50 |
| | 5 | Ethyl acetate | 20 | 1 | 0 | 19 | 5 |

Example 12

Figure 8:
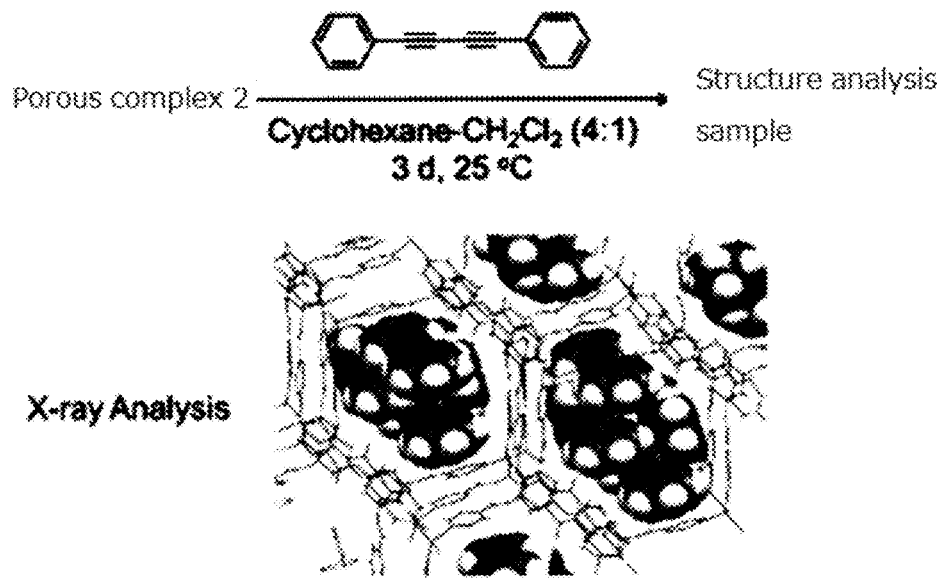
FIG. 8 illustrates a result of crystal structure analysis in Example 11.

A crystal judged as Grade A in Example 7 was immersed in a mixed solution of 1,4-diphenylbutadiyne in cyclohexane and dichloromethane (4:1) at room temperature (25° C.) for 3 days. The resultant crystal structure analysis sample was used for performing crystal structure analysis. The results are shown in Table 5 and FIG. 8.

TABLE 5

| Crystal system | Monoclinic |
|---|---|
| Space groups | C2/c |
| a (Å) | 63.947 |
| b (Å) | 15.511 |
| c (Å) | 30.015 |
| α (°) | 90 |
| β (°) | 113.73 |
| γ (°) | 90 |
| Z | 8 |
| R1 (%) | 11.47 |

Example 13

Confirmation Test of Single Crystallinity (Measurement of Shape Retention Ratio (1))

A crystal of a porous complex 1, which was brought into contact with an appropriate solvent, was placed in a petri dish, and a tungsten steel needle for manipulating the crystal manufactured by HAMPTON RESEARCH CORP. (needle diameter=0.1 mm) was brought into contact with the single crystal, and then the single crystal was subjected to 10 mm parallel shift by exerting a force of $10^{-2}$ N or less, and then the parallel shifted single crystal was checked by optical microscopic observation to prove whether the shape of the crystal was retained.

Figure 9:
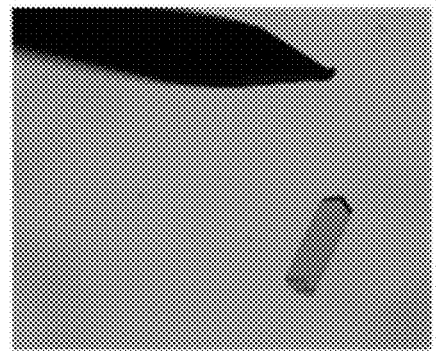
FIG. 9 shows photographic images derived from observation of a crystal before and after the measurement of shape retention ratio (1) of Case 1 in Example 13.
Figure 9:
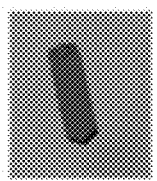

As shown in FIG. 9 (Case 1), when shape retention ratio (1) was 90% or more (100%), it could be determined that the crystal was appropriate for immersion in a guest solution as a crystalline sponge, and for an X-ray crystal structure analysis.

Comparative Example 3

Figure 10:
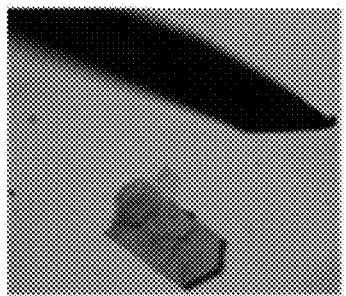
FIG. 10 shows photographic images derived from observation of a crystal before and after the measurement of shape retention ratio (1) of Case 2 in Comparative Example 3.
Figure 10:
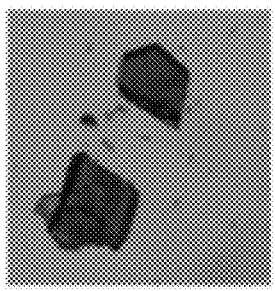

On the other hand, when a crystal having a crack (a crystal of a porous complex 1) as shown in FIG. 10 (Case 2) was subjected to a parallel shift operation in a similar manner, shape retention ratio (1) was 10% or less (9%), and thus it was determined that the crystal could not be used as a crystalline sponge.

Example 14

Confirmation Test of Single Crystallinity (Measurement of Shape Retention Ratio (2))

A crystal of a porous complex 1, which was brought into contact with an appropriate solvent, was placed in a petri dish, and using a micropipet (Nichipet EX Plus II) manufactured by NICHIRYO CO., LTD. and a pipet tip (manufactured by AS ONE Corporation Friend Tips for 20 to 200 μL, aperture of 250 μm in diameter), the crystal was subjected to a suction operation. The suction rate of the crystal was at 6 μL/sec. After the operation, as shown in FIG. 11 (Case 3), when shape retention ratio (1) as defined above was 90% or more (98%), it could be determined that the crystal could be used for the following immersion in a guest solution, and for X-ray crystal structure analysis.

Comparative Example 4

Figure 12:
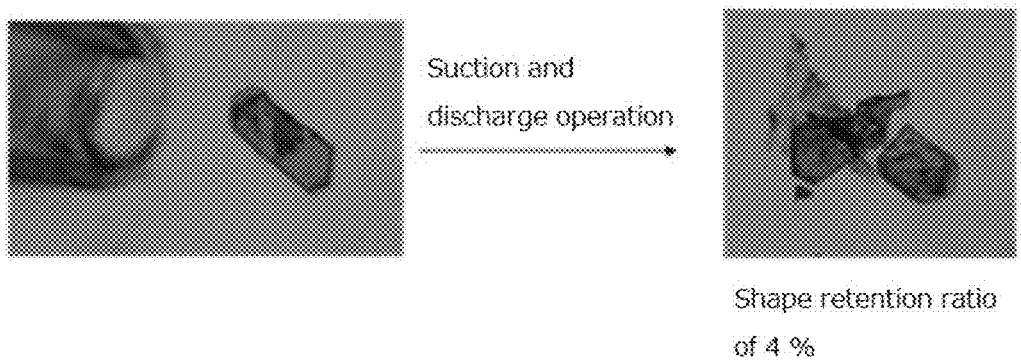
FIG. 12 shows photographic images derived from observation of a crystal before and after the measurement of shape retention ratio (2) of Case 4 in Comparative Example 4.

On the other hand, when a crystal having a crack (a crystal of a porous complex 1) as shown in FIG. 12 (Case 4) was subjected to a suction and discharge operation in a similar manner, shape retention ratio (2) was 10% or less, and thus it was determined that the crystal could not be used as a crystalline sponge.

Example 15, and Comparative Example 5

Further, a judgement similar to that described above can be applied to other porous complexes used for the crystalline sponge method. For example, examples with respect to a porous complex 2 are provided below.

(1) Measurement of Shape Retention Ratio (1) of Porous Complex 2

Figure 13:
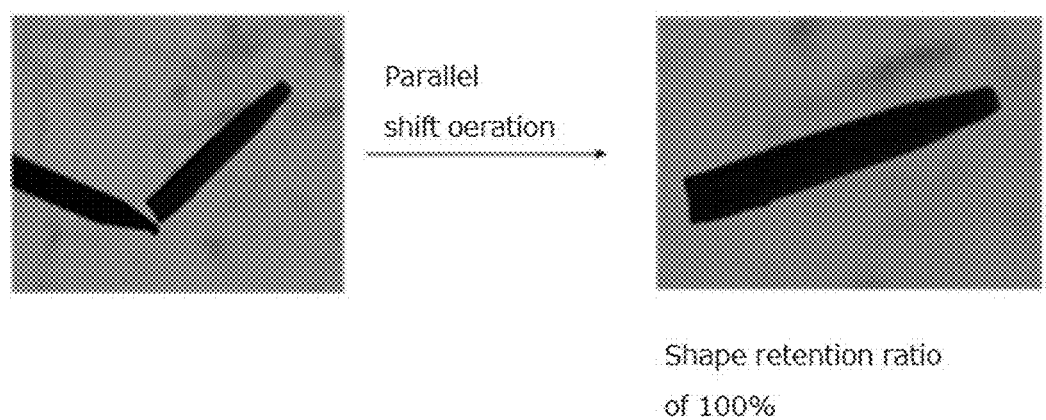
FIG. 13 shows photographic images derived from observation of a crystal before and after the measurement of shape retention ratio (1) of Case 5 in Example 15.

(i) FIG. 13 (Case 5) shows an example of a crystal which shows a high shape retention ratio (1) (Example 15).

Figure 14:
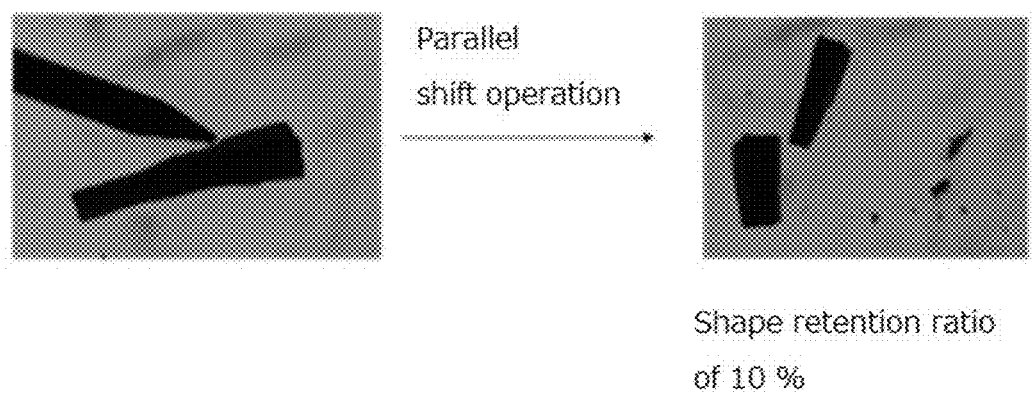
FIG. 14 shows photographic images derived from observation of a crystal before and after the measurement of shape retention ratio (1) of Case 6 in Comparative Example 5.

(ii) FIG. 14 (Case 6) shows an example of a crystal which shows a low shape retention ratio (1), and is unusable (Comparative Example 5).

Example 16, Comparative Example 6

(2) Measurement of Shape Retention Ratio (2) of a Porous Complex 2

Figure 15:
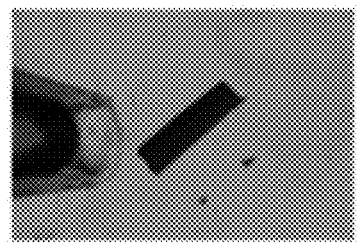
FIG. 15 shows photographic images derived from observation of a crystal before and after the measurement of shape retention ratio (2) of Case 7 in Example 16.
Figure 15:
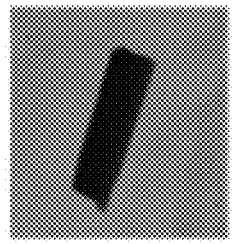

(i) FIG. 15 (Case 7) shows an example of a crystal which shows a high shape retention ratio (2) (Example 16).

Figure 16:
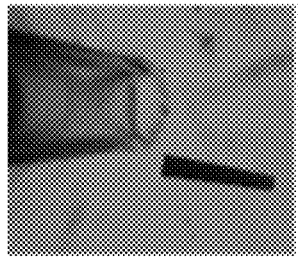
FIG. 16 shows photographic images derived from observation of a crystal before and after the measurement of shape retention ratio (2) of Case 8 in Comparative Example 6.
Figure 16:
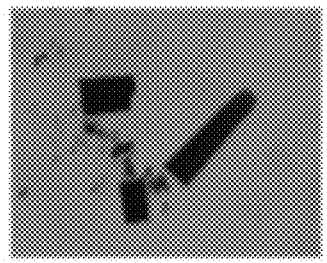

(ii) FIG. 16 (Case 8) shows an example of a crystal which shows a low shape retention ratio (2), and thus is unusable (Comparative Example 6).

Color copies of FIGS. 2, 3, and 5 to 16 will be submitted as submission materials separately from the present specification.

REFERENCE SIGNS LIST

1: Crystal plane X
2: Crystal plane Y
3: Pore
4: Extension direction of pore

The invention claimed is:

1. A method for determination of whether a single crystal used for producing a crystal structure analysis sample of an analysis target compound is good or bad by bringing a porous compound single crystal having a three-dimensional framework, and having pores and/or voids, which are defined by the three-dimensional framework, that are three-dimensionally arranged in an ordered manner into contact with an analysis target compound-containing solution to arrange molecules of the analysis target compound in the pores and/or the voids in an ordered manner, the method comprising
   step (A1): bringing the single crystal into contact with a solvent which is chemically identical to a solvent of the analysis target compound-containing solution; and
   step (A2): when the single crystal is confirmed to maintain single crystallinity even after the contact of the single crystal with the solvent in step (A1), determining the single crystal as suitable for producing the crystal structure analysis sample,
   wherein the method for confirming the single crystal as maintaining single crystallinity in step (A2) comprises:
      (i) confirming an absence of color irregularities or brightness irregularities in the porous compound single crystal by crossed Nicols observation of the porous compound single crystal using a polarization microscope, dimensionally arranged in an ordered manner into contact with the analysis target compound-containing solution to arrange molecules of the analysis target compound in the pores and/or the voids in an ordered manner, the method comprising step (B1): bringing the single crystal into contact with a solvent dissolving the analysis target compound, and step (B2): when the single crystal is confirmed to maintain single crystallinity even after the contact of the single crystal with the solvent in step (B1), determining the solvent as suitable for a solvent of the analysis target compound-containing solution used for producing the crystal structure analysis sample, wherein the method for determining the solvent as suitable for the solvent of the analysis target compound-containing solution used for producing the crystal structure analysis sample in step (B2) comprises:

(v) confirming an absence of color irregularities or brightness irregularities in the porous compound single crystal by crossed Nicols observation of the porous compound single crystal using a polarization microscope, (vi) confirming that a rate of change in absorbance of UV-vis absorption spectrum of the single crystal within a wavelength range of 450 to 500 nm is 10% or less between before and after bringing the single crystal into contact with a solvent which is chemically identical to the solvent of the analysis target compound-containing solution, (vii) confirming that shape retention ratio of the single crystal is 90% or more between before and after an operation of 10 mm parallel shift of the single crystal by exerting a force of $10^{-2}$ N or less on the single crystal using a tungsten steel needle for manipulating the crystal (ii) confirming that a rate of change in absorbance of UV-vis absorption spectrum of the single crystal within a wavelength range of 450 to 500 nm is 10% or less between before and after bringing the single crystal into contact with the solvent which is chemically identical to the solvent of the analysis target compound-containing solution, (iii) confirming that shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in the solvent which is chemically identical to the solvent of the analysis target compound-containing solution at a liquid depth of 5 mm, or (iv) confirming that shape retention ratio of the single crystal is 90% or more between before and after an operation of sucking a solution containing the single crystal and the solvent which is chemically identical to the solvent of the analysis target compound-containing solution at a suction rate of 6 μL/sec using a pipet tip for 20 to 200 μL having an aperture of 250 μm in diameter at a liquid depth of 5 mm, and then discharging the solution containing the single crystal at a discharge rate of 6 μL/sec.

2. A method for preparing an analysis target compound-containing solution used for producing a crystal structure analysis sample of the analysis target compound by bringing a porous compound single crystal having a three-dimensional framework, and having pores and/or voids, which are defined by the three-dimensional framework, that are three- (needle diameter=0.1 mm) in a solvent which is chemically identical to the solvent of the analysis target compound-containing solution at a liquid depth of 5 mm, or (viii) confirming that shape retention ratio of the single crystal is 90% or more between before and after an operation of sucking a solution containing the single crystal and a solvent which is chemically identical to the solvent of the analysis target compound-containing solution at a suction rate of 6 μL/sec using a pipet tip for 20 to 200 μL having an aperture of 250 μm in diameter at a liquid depth of 5 mm, and then discharging the solution containing the single crystal at a discharge rate of 6 μL/sec.

3. A method for producing a crystal structure analysis sample, comprising bringing a single crystal, which is confirmed to maintain single crystallinity by the method according to claim 1, contact with an analysis target compound-containing solution to arrange molecules of an analysis target compound in the pores and/or the voids in an ordered manner.

4. A method for determining a molecular structure of an analysis target compound, comprising performing crystal structure analysis using a crystal structure analysis sample obtained by a method for producing the crystal structure analysis sample according to claim 3.

5. The method for determination of whether a single crystal used for producing a crystal structure analysis sample of an analysis target compound is good or bad according to claim 1, wherein a length of one side of the single crystal is 10 to 2000 μm.

6. The method for determination of whether a single crystal used for producing a crystal structure analysis sample of an analysis target compound is good or bad according to claim 5, wherein the analysis target compound-containing solution is obtained by:

step (B1): bringing the single crystal into contact with a solvent dissolving the analysis target compound, and step (B2): when the single crystal is confirmed to maintain single crystallinity even after the contact of the single crystal with the solvent in step (B1), determining the solvent as suitable for a solvent of the analysis target compound-containing solution used for producing the crystal structure analysis sample, wherein the method for determining the solvent as suitable for the solvent of the analysis target compound-containing solution used for producing the crystal structure analysis sample in step (B2) comprises:

(v) confirming an absence of color irregularities or brightness irregularities in the porous compound single crystal by crossed Nicols observation of the porous compound single crystal using a polarization microscope, (vi) confirming that a rate of change in absorbance of UV-vis absorption spectrum of the single crystal within a wavelength range of 450 to 500 nm is 10% or less between before and after bringing the single crystal into contact with a solvent which is chemically identical to the solvent of the analysis target compound-containing solution, (vii) confirming that shape retention ratio of the single crystal is 90% or more between before and after an operation of 10 mm parallel shift of the single crystal by exerting a force of $10^{-2}$ N or less on the single crystal using a tungsten steel needle for manipulating the crystal (needle diameter=0.1 mm) in a solvent which is chemically identical to the solvent of the analysis target compound-containing solution at a liquid depth of 5 mm, or (viii) confirming that shape retention ratio of the single crystal is 90% or more between before and after an operation of sucking a solution containing the single crystal and a solvent which is chemically identical to the solvent of the analysis target compound-containing solution at a suction rate of 6 µL/sec using a pipet tip for 20 to 200 µL having an aperture of 250 µm in diameter at a liquid depth of 5 mm, and then discharging the solution containing the single crystal at a discharge rate of 6 µL/sec.

7. The method for preparing an analysis target compound-containing solution according to claim 2,
wherein a length of one side of the single crystal is 10 to 2000 µm.

* * * * *